United States Patent
Shen et al.

(10) Patent No.: US 11,458,417 B2
(45) Date of Patent: Oct. 4, 2022

(54) METHOD FOR SEPARATING EIGHTEEN COMPONENTS IN TRADITIONAL CHINESE MEDICINE COMPOSITION

(71) Applicant: SHIJIAZHUANG YILING PHARMACEUTICAL CO., LTD., Hebei (CN)

(72) Inventors: Shuo Shen, Hebei (CN); Chuangfeng Zhang, Hebei (CN); Dan Bi, Hebei (CN); Feng Wei, Hebei (CN); Yunbo Sun, Hebei (CN)

(73) Assignee: SHIJIAZHUANG YILING PHARMACEUTICAL CO., LTD., Hebei (CN)

( * ) Notice: Subject to any disclaimer, the term of this patent is extended or adjusted under 35 U.S.C. 154(b) by 362 days.

(21) Appl. No.: 16/643,632

(22) PCT Filed: Sep. 5, 2018

(86) PCT No.: PCT/CN2018/104148
§ 371 (c)(1),
(2) Date: Mar. 2, 2020

(87) PCT Pub. No.: WO2019/047848
PCT Pub. Date: Mar. 14, 2019

(65) Prior Publication Data
US 2020/0398188 A1 Dec. 24, 2020

(30) Foreign Application Priority Data
Sep. 5, 2017 (CN) .......................... 201710789895.5

(51) Int. Cl.
*A61K 36/00* (2006.01)
*B01D 15/26* (2006.01)
*A61K 36/63* (2006.01)

(52) U.S. Cl.
CPC ............ *B01D 15/265* (2013.01); *A61K 36/63* (2013.01); *A61K 2236/55* (2013.01)

(58) Field of Classification Search
None
See application file for complete search history.

(56) References Cited

FOREIGN PATENT DOCUMENTS

CN  1631895 A  6/2005

OTHER PUBLICATIONS

English translation of International Search Report for International Application No. PCT/CN2018/104148, dated Dec. 4, 2018, 3 pages.
Wang, F. N. et al., New Phenylethanoid Glycosides from the Fruits of Forsythia Suspense (Thunb.) Vahl, Molecules, Mar. 25, 2009, vol. 14, No. 3, pp. 1324-1331.
Li, H. M. et al., Analysis of the Inhibitory Activity of Abeliophyllum Distichum Leaf Constituents against Aldose Reductase by Using High-Speed Counter Current Chromatography, Arch. Pharm. Res., May 5, 2013, vol. 36, No. 9, pp. 1104-1112. Abstract only.
Song, S. et al., Concurrent Quantification and Comparative Pharmacokinetic Analysis of Bioactive Compounds in the Herba Ephedrae-Semen Armeniacae Amarum Herb Pair, Journal of Pharmaceutical and Biomedical Analysis, Feb. 14, 2015, vol. 109, pp. 67-73. Abstract only.
Xia, Y. G. et al., Caffeoyl Phenylethanoid Glycosides from Unripe Fruits of Forsythia Suspensa, Chemistry of Natural Compounds, Jul. 31, 2015, vol. 51, No. 4, pp. 656-659. Abstract only.
Fan, Y. et al., Chemical Constituents of Leaves of Forsythia Suspense, Chinese Journal of Experimental Traditional Medical Formulae, Dec. 31, 2015, vol. 21, No. 24, pp. 22-25. Abstract only.

*Primary Examiner* — Michael V Meller
(74) *Attorney, Agent, or Firm* — Armstrong Teasdale LLP

(57) ABSTRACT

The disclosure provides a method for separating eighteen components in a traditional Chinese medicine composition, including: (1) preparing the traditional Chinese medicine composition into a total extract of the traditional Chinese medicine composition, separating by resin through sequentially eluting with water, 10% ethanol and 30% ethanol, and collecting the 30% ethanol eluate to obtain a 30% ethanol extract; (2) adding the 30% ethanol extract to a reverse phase silica gel ODS-AQ-HG, and separating in a medium pressure separation column to obtain differently numbered elution dry pastes; (3) dissolving the differently numbered elution dry paste with 30% methanol as a solvent, and passing the solution through a 0.45 μm microporous membrane, carrying out a primary separation by high performance liquid chromatography and collecting chromatographic peaks with different retention times, and further purifying by high performance liquid chromatography; finally obtaining the components of eighteen components.

1 Claim, No Drawings

METHOD FOR SEPARATING EIGHTEEN COMPONENTS IN TRADITIONAL CHINESE MEDICINE COMPOSITION

CROSS-REFERENCE TO RELATED APPLICATIONS

This application is a U.S. National Phase Application of PCT/CN2018/104148, filed Sep. 5, 2018, which claims the benefit of priority to CN Application No. 201710789895.5, filed Sep. 5, 2017, the contents of which are hereby expressly incorporated by reference in their entirety.

TECHNICAL FIELD

The invention belongs to the field of quality analysis and control of traditional Chinese medicine, and specifically relates to a method for separating eighteen components in traditional Chinese medicine composition.

BACKGROUND OF ART

The traditional Chinese medicine compound is the main form of traditional Chinese medicine. After thousands of years of clinical use, the compound can obtain a stronger therapeutic effect than a single medicine, which has fully proved the scientific nature of the compound composition.

A pharmaceutical composition consisting of 13 traditional Chinese medicines, such as *Fructus Forsythiae*, *Flos Lonicerae* and *Herba Ephedrae*, has the function of clearing distemper and detoxifying, ventilating lung and releasing heat. Clinical studies have confirmed that the pharmaceutical composition has a definite and significant effect on treating influenza and acute upper respiratory infections.

In order to clarify the pharmacological action mechanism of this compound and the scientific connotation of the compatibility regulation of compounded drugs, it is necessary to conduct a systematic study on its fundamentals of substances.

SUMMARY OF THE PRESENT INVENTION

The objective of the present invention is to provide a method for separating eighteen components in a traditional Chinese medicine composition, on which the problem to be solved is that it is difficult to achieve rapid separation of high polar components because of the diversity of chemical components and the complex chemical structure of traditional Chinese medicine compounds. The composite reverse rapid separation technology can effectively separate the large polar components of the traditional Chinese medicine composition in a short time, and obtain a series of representative compounds.

In order to achieve the above objective, a method for separating eighteen components in a traditional Chinese medicine composition is provided, the traditional Chinese medicine composition is made from crude drugs with the following part by weight: *Fructus Forsythiae* 200-300, *Herba Ephedrae* 60-100, *Radix et Rhizoma Rhei* 40-60, *Herba Houttuyniae* 200-300, *Flos Lonicerae* 200-300, *Radix Isatidis* 200-300, *Herba Pogostemonis* 60-100, *Rhizoma Dryopteris Crassirhizomae* 200-300, *Radix Rhodiolae* 60-100, menthol 5-9, *Semen Armeniacae Amarum* 60-100, *Radix Glycyrrhizae* 60-100, *Gypsum Fibrosum* 200-300, wherein the method for separating includes the following steps:

(1) the total extract of the traditional Chinese medicine composition is separated by AB-8 macroporous resin, and then eluted with water, 10% ethanol, and 30% ethanol in sequence, and then the 30% ethanol eluate is collected and the solvent is recovered to obtain a 30% ethanol extract;

(2) the 30% ethanol extract obtained in step (1) is loaded to the reversed-phase silica gel ODS-AQ-HG, S-50 μm, and mixed; after a mixed ODS is naturally dried, the mixed ODS is loaded to a sample column and the medium pressure preparation liquid phase is loaded for separation, the separation column packing is ODS-AQ-HG, S-50 μm; successively 10% methanol is used, 5 fractions are obtained in order of elution, and numbers thereof are 10%-1, 10%-2, 10%-3, 10%-4, 10%-5; 20% methanol is used for eluting, 6 fractions are obtained in order of elution, and numbers thereof are 20%-1, 20%-2, 20%-3, 20%-4, 20%-5, and 20%-6; the eluate is collected and the solvent is recovered respectively, and eluting dry extracts which are numbered 10%-1, 10%-2, 10%-3, 10%-4, 10%-5 and eluting dry extracts which are numbered 20%-1, 20%-2, 20%-3, 20%-4, 20%-5 and 20%-6 are obtained;

(3) the 10%-1 eluting dry extract obtained in step (2) is dissolved with 30% methanol, and the solution is filtered through a 0.45 μm microporous membrane and preliminarily separated by high-performance liquid chromatography; the mobile phase is methanol-water 22:78, the flow rate is 1 ml/min, the detection wavelength is 210 nm; chromatographic peaks with retention time of 3-9 min, 9-11 min, 19-22 min, 22-26 min, 26-30 min, 37-41 min and 44-48 min are collected, and the solvent is recovered under reduced pressure, and the following separations are performed respectively:

3-9 min chromatographic peak: being further purified by high performance liquid chromatography, mobile phase: methanol-water, 5:95, flow rate: 10 ml/min, detection wavelength 210 nm, chromatographic column: YMC-Pack R & D ODS-A, 250×20 mm, S-10 μm; under these conditions, the chromatographic peak with retention time of 25-27 min is collected, and the solvent is recovered under reduced pressure to obtain compound 14: Cornoside;

9-11 min chromatographic peak: being further purified by high performance liquid chromatography, mobile phase: methanol-water, 12:88, flow rate: 10 ml/min, detection wavelength 210 nm, chromatographic column: YMC-Pack R & D ODS-A, 250×20 mm, S-10 μm; under these conditions, the chromatographic peak with retention time of 32-35 min is collected, and the solvent is recovered under reduced pressure to obtain compound 10: Ferruginoside B;

19-22 min chromatographic peak: being further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 μm; under these conditions, the chromatographic peak with a retention time of 31-35 min is collected, and the solvent is recovered under reduced pressure to obtain compound 9: Forsythoside E;

22-26 min chromatographic peak: being further purified by high performance liquid chromatography, mobile phase: methanol-water, 16:84, flow rate: 10 ml/min, detection wavelength 210 nm, chromatographic column: YMC-Pack R & D ODS-A, 250×20 mm, S-10 μm; under these conditions, the chromatographic peak with a retention time of 32-37 min is collected, and the solvent is recovered under reduced pressure to obtain compound 18: 3,4-dihydroxybenzaldehyde;

26-30 min chromatographic peak: being further purified by high performance liquid chromatography, mobile phase:

methanol-water, 18:82, flow rate: 10 ml/min, detection wavelength 210 nm, chromatographic column: YMC-Pack R & D ODS-A, 250×20 mm, S-10 μm; under these conditions, the chromatographic peak with a retention time of 38-42 min is collected, and the solvent is recovered under reduced pressure to obtain a mixture of compound 11: D-Amygdalin and compound 12: L-Amygdalin;

37-41 min chromatographic peak: being further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 μm; under these conditions, the chromatographic peak with a retention time of 52-56 min is collected, and the solvent is recovered under reduced pressure to obtain compound 13: Sambunigrin;

44-48 min chromatographic peak: being further purified by high performance liquid chromatography, mobile phase: methanol-water, 22:78, flow rate: 10 ml/min, detection wavelength 210 nm, chromatographic column: YMC-Pack R & D ODS-A, 250×20 mm, S-10 μm; under these conditions, the chromatographic peak with a retention time of 41-44 min is collected, and the solvent is recovered under reduced pressure to obtain compound 15: 4-Hydroxy-4-methylenecarbomethoxy-cyclohexa-2,5-dienone;

(4) the 20%-2 eluting dry extract obtained in step (2) is dissolved in 30% methanol and filtered through a 0.45 μm microporous filter membrane, and high-performance liquid chromatography is used for preliminary separation; mobile phase is methanol-water, 22:78, flow rate: 10 ml/min, detection wavelength 210 nm, chromatographic column: YMC-Pack R & D ODS-A, 250×20 mm, S-10 μm; chromatographic peaks with retention time of 14-17 min, 17-19 min, 22-24 min, 29-34 min, and 35-40 min are collected, and the solvent is recovered under reduced pressure, and the following separations are performed respectively:

14-17 min chromatographic peak: being further purified by high performance liquid chromatography, mobile phase: acetonitrile-water, 15:85, flow rate: 10 ml/min, detection wavelength 210 nm, chromatographic column: YMC-Pack R & D ODS-A, 250×20 mm, S-10 μm; under these conditions, the chromatographic peaks with retention time of 38-40 min and 45-47 min are collected, the solvent in 45-47 min chromatographic peaks is recovered under reduced pressure to obtain compound 7: Lianqiaoxingan C; the solvent in 38-40 min chromatographic peaks is recovered under reduced pressure and then purified by high performance liquid chromatography, the mobile phase: acetonitrile-water, 13:87, the flow rate: 10 ml/min, and the detection wavelength: 210 nm, chromatographic column: 250×20 mm, S-10 μm, under this condition, the chromatographic peak with retention time of 52-56 min is collected, and the solvent is recovered under reduced pressure to obtain compound 6: Ferruginoside A;

17-19 min chromatographic peak: being further purified by high performance liquid chromatography, mobile phase: acetonitrile-water, 15:85, flow rate: 10 ml/min, detection wavelength 210 nm, chromatographic column: YMC-Pack R & D ODS-A, 250×20 mm, S-10 μm; under these conditions, chromatographic peaks with retention time of 28-30 min and 37-44 min are collected, and the solvent is recovered under reduced pressure to obtain compound 16: Liriodendrin and compound 2: Forsythoside I respectively;

22-24 min chromatographic peak: being further purified by high performance liquid chromatography, mobile phase: acetonitrile-water, 17:83, flow rate: 10 ml/min, detection wavelength 210 nm, chromatographic column: YMC-Pack R & D ODS-A, 250×20 mm, S-10 μm; under these conditions, the chromatographic peak with a retention time of 22-25 min is collected, and the solvent is recovered under reduced pressure to obtain compound 8: Calceolarioside C;

29-34 min chromatographic peak: after recovering the solvent under reduced pressure, white solids are precipitated after the solvent being evaporated during the standing process, and centrifuged at 5000 rpm to obtain compound 17: glycyrrhizin-7-O-β-D-glucoside; supernatant is further purified by high performance liquid chromatography, mobile phase: acetonitrile-water, 16:84, flow rate: 10 ml/min, detection wavelength 210 nm, chromatographic column: YMC-Pack R & D ODS-A, 250×20 mm, S-10 μm; under these conditions, the chromatographic peak with retention time of 40-45 min is collected, and the solvent is recovered under reduced pressure to obtain compound 3: Forsythoside H;

35-40 min chromatographic peak: being further purified by high performance liquid chromatography, mobile phase: acetonitrile-water, 16:84, flow rate: 10 ml/min, detection wavelength 210 nm, chromatographic column: YMC-Pack R & D ODS-A, 250×20 mm, S-10 μm; under these conditions, the chromatographic peak with retention time of 34-45 min is collected, and the solvent is recovered under reduced pressure to obtain compound 1: Forsythoside A;

(5) the fraction 20%-4 and fraction 20%-5 obtained in step (2) are mixed, and is dissolved with 30% methanol and filtered through a 0.45 μm microporous membrane, and high-performance liquid chromatography is used for preliminary separation; mobile phase: acetonitrile-water, 15:85, flow rate: 15 ml/min, detection wavelength 210 nm, chromatographic column: YMC-Pack R & D ODS-A, 250×20 mm, S-10 μm; chromatographic peaks with retention time of 15-17 and 35-40 min are collected, and the solvent is recovered under reduced pressure; wherein, 15-17 min chromatographic peaks: being further purified by high performance liquid chromatography, mobile phase: acetonitrile-water, 15:85, flow rate: 12 ml/min, detection wavelength 210 nm, chromatographic column: YMC-Pack R & D ODS-A, 250×20 mm, S-10 μm; under these conditions, chromatographic peak with retention time of 15-16 min is collected, and the solvent is recovered under reduced pressure to obtain compound 5: Isolugrandoside;

35-40 min chromatographic peak: being further purified by high performance liquid chromatography, mobile phase: methanol-water, 25:75, flow rate: 12 ml/min, detection wavelength 210 nm, chromatographic column: YMC-Pack R & D ODS-A, 250×20 mm, S-10 μm; under these conditions, the chromatographic peak with retention time of 26-29 min is collected, and the solvent is recovered under reduced pressure to obtain compound 4: Lugrandoside.

In the present invention, (1) the concentration of methanol and ethanol used in each separation step are both volume concentration (vol %); (2) the amount ratio of the methanol-water, the amount ratio of the acetonitrile-water used as the mobile phase for preliminary separation by high-performance liquid chromatography are all volume ratios; (3) the chromatographic peak of each retention time collected after preliminary separation by high-performance liquid chromatography is further purified and separated by high-performance liquid chromatography, means that the samples obtained from the fractions corresponding to each chromatographic peak with retention time after the solvent recovery are further purified.

According to the method for separating eighteen components provided by the present invention, preferably, in the step (1), the amounts of the eluent water, 10% ethanol, and 30% ethanol are 40 ml eluent water, 17.6 ml 10% ethanol, 45 ml 30% ethanol for 1 g the total extract of Chinese medicine composition.

According to the method for separating eighteen components provided by the present invention, preferably, the amount of the reversed-phase silica gel ODS-AQ-HG in step (2) is: 8 g of the reversed-phase silica gel ODS-AQ-HG for 1 g of 30% ethanol extract obtained in step (1), wherein 3 g is used for mixing with 1 g of 30% ethanol extract obtained in step (1), and 5 g is used as the packing for the medium pressure separation column.

Preferably, in step (2), successively 10% methanol is used; 5 fractions are obtained in order of elution, and the amount of eluent for each fraction is: 66.7 ml of 10% methanol for 1 g of 30% ethanol extract obtained in step (1); 20% methanol is used for eluting, 6 fractions are obtained in order of elution, and the amount of eluent for each fraction is: 44.4-66.7 ml of 20% methanol for 1 g of 30% ethanol extract obtained in step (1).

According to the method for separating eighteen components provided by the present invention, preferably, the traditional Chinese medicine composition is made from crude drugs with the following part by weight:

Fructus Forsythiae 200, Flos Lonicerae 300, Radix Isatidis 200, Radix et Rhizoma Rhei 40, Herba Pogostemonis 60, Rhizoma Dryopteris Crassirhizomae 300, Radix Rhodiolae 100, menthol 9, Herba Ephedrae 60, Semen Armeniacae Amarum 100, Herba Houttuyniae 200, Radix Glycyrrhizae 100, Gypsum Fibrosum 200.

Preferably, the traditional Chinese medicine composition is made from crude drugs with the following part by weight:

Fructus Forsythiae 300, Flos Lonicerae 200, Radix Isatidis 300, Radix et Rhizoma Rhei 60, Herba Pogostemonis 100, Rhizoma Dryopteris Crassirhizomae 200, Radix Rhodiolae 60, menthol 5, Herba Ephedrae 100, Semen Armeniacae Amarum 60, Herba Houttuyniae 300, Radix Glycyrrhizae 60, Gypsum Fibrosum 300.

Preferably, the traditional Chinese medicine composition is made from crude drugs with the following part by weight:

Fructus Forsythiae 278, Flos Lonicerae 294, Radix Isatidis 285, Radix et Rhizoma Rhei 55, Herba Pogostemonis 95, Rhizoma Dryopteris Crassirhizomae 290, Radix Rhodiolae 87, menthol 8.5, Herba Ephedrae 88, Semen Armeniacae Amarum 80, Herba Houttuyniae 284, Radix Glycyrrhizae 95, Plaster 277.

According to the method for separating eighteen components provided by the present invention, preferably, the total extract of the traditional Chinese medicine composition is made by the following steps:

(1) the crude drugs are weighed according to the weight ratio, chosen for the clean ones and ground;
(2) the Herba Pogostemonis is ground, 10 times amount of water is added to extract the volatile oil, and extraction time of the volatile oil is 8 hours, and then the volatile oil is collected and is reserved for use; after the extract is filtered, the residue is discarded and the filtrate is reserved for use;
(3) Fructus Forsythiae, Herba Ephedrae, Herba Houttuyniae, and Radix et Rhizoma Rhei are extracted with 12 times amount of 70% ethanol for 3 times, 2.5 hours each time; extracts are mixed and filtrated, the ethanol is recovered, and filtrate is reserved for use;
(4) Flos Lonicerae, Gypsum Fibrosum, Radix Isatidis, Rhizoma Dryopteris Crassirhizomae, Radix Glycyrrhizae and Radix Rhodiolae are boiled in 12 times amount of water, then the Semen Armeniacae Amarum is added and boiled twice, 1 hour each time; extracts are mixed and filtered, and filtrate obtained is combined with the filtrate obtained after extracting Herba Pogostemonis in step (2), and condensed into a clear extract having a relative density of 1.10-1.15 at 60° C., and then ethanol is added to adjust alcohol concentration to be 70%, refrigerated (for example, 4° C.), filtered, and the ethanol is recovered until no alcohol taste, the clear extract is obtained and reserved for use;
(5) the clear extract obtained in step (4) is combined with the alcohol extract obtained in step (3), and then condensed into a clear extract having relative density of 1.15-1.20 at 60° C.; dried to obtain total extract and reserved for use.

The pharmaceutical composition of the present invention is made from 13 kinds of traditional Chinese medicines, such as Fructus Forsythiae, Flos Lonicerae and Herba Ephedrae, which has the functions of clearing distemper and detoxifying, ventilating lung and releasing heat, and is used for treating influenza. It has a definite and significant effect on treating influenza and acute upper respiratory infections. In order to elucidate the pharmacological action mechanism of this compound and the scientific connotation of the compatibility regulation of compounded drugs, it is necessary to conduct a systematic study on its fundamentals of substances.

In view of the above, the chemical ingredients of the pharmaceutical composition according to the present invention was studied deeply (see Patent No. CN1483463 A for details), and 18 components are separated and identified in the 30% ethanol portion from the macroporous adsorption resin column of its total extract. 18 compounds are Forsythoside A (1), Forsythoside I (2), Forsythoside H (3), Lugrandoside (4), Isolugrandoside (5), Ferruginoside A (6), Lianqiaoxingan C (7), Calceolarioside C (8), Forsythoside E (9), Ferruginoside B (10), D-Amygdalin (11), L-Amygdalin (12), Sambunigrin (13), Cornoside (14), 4-Hydroxy-4-methylenecarbomethoxy-cyclohexa-2,5-dienone (15), Liriodendrin (16), glycyrrhizin-7-O-β-D-glucoside (17), 3,4-diHydroxybenzaldehyde (18), respectively.

Among them, compound 2 to compound 8, compound 10, compound 13 to compound 18 are separated from the total extract described in the present invention for the first time; there is no report on the separation of compound 4 to compound 6, compound 10, compound 15 and compound 16 from any single drug in the compound drugs, and the nuclear magnetic data of compound 8 in DMSO-d6 solvent is assigned for the first time.

The beneficial effects of the technical solution in the present invention lie in:
(1) macroporous resin adsorption column chromatography, reversed-phase low-pressure column chromatography, and high-pressure preparative liquid chromatography technology are combined to achieve effective separation of large polar components in the traditional Chinese medicine composition;
(2) the technical solution in the present invention has high separation efficiency of the chemical components of the traditional Chinese medicine composition, and a representative monomer compound in the compound drugs can be obtained in a short time;
(3) compared with the prior technology using a single silica gel column chromatography, the technical solution in the present invention has less consumption of organic reagents and less environmental pollution during the separation process.

EMBODIMENT

In order to understand the technical features and contents of the present invention in detail, preferred embodiments of the present invention will be described in more detail below. Although the preferred embodiments of the present invention are described in the examples, it should be understood that the present invention can be implemented in various forms and should not be limited by the embodiments set forth herein.

In an embodiment of the present invention, the method for separating eighteen components in a traditional Chinese medicine composition is provided, the traditional Chinese medicine composition is made from crude drugs with the following part by weight: *Fructus Forsythiae* 200-300, *Herba Ephedrae* 60-100, *Radix* et *Rhizoma Rhei* 40-60, *Herba Houttuyniae* 200-300, *Flos Lonicerae* 200-300, *Radix Isatidis* 200-300, *Herba Pogostemonis* 60-100, *Rhizoma Dryopteris Crassirhizomae* 200-300, *Radix Rhodiolae* 60-100, menthol 5-9, *Semen Armeniacae Amarum* 60-100, *Radix Glycyrrhizae* 60-100, *Gypsum Fibrosum* 200-300, wherein the method for separating includes the following steps:

(1) the traditional Chinese medicine composition is prepared into total extract, and then the total extract of the traditional Chinese medicine composition is separated by AB-8 macroporous resin, and then eluted with water, 1 vol. % ethanol, and 30 vol. % ethanol in sequence, and then the 30 vol. % ethanol eluate is collected and the solvent is recovered to obtain a 30% ethanol extract;

(2) the 30% ethanol extract obtained in step (1) is loaded to the reversed-phase silica gel ODS-AQ-HG, S-50 μm and mixed ODS is obtained by mixing; after a mixed ODS is naturally dried, the mixed ODS is loaded to a sample column (for example, its length is 8 cm and its diameter is 4 cm) and the medium pressure preparation liquid phase is used for separation, the intermediate pressure separation column (for example, 40 cm in length and 5 cm in diameter) is packed with ODS-AQ-HG, S-50 μm; first, 10 vol. % methanol is used, 5 fractions are obtained in order of elution, and numbers thereof are 10%-1, 10%-2, 10%-3, 10%-4, 10%-5; then, 20 vol. % methanol is used for eluting, 6 fractions are obtained in order of elution, and numbers thereof are 20%-1, 20%-2, 20%-3, 20%-4, 20%-5, and 20%-6; 10% methanol eluent and 20% methanol eluent are collected respectively and the solvent is recovered respectively, and eluting dry extracts which are numbered 10%-1, 10%-2, 10%-3, 10%-4, 10%-5 and eluting dry extracts which are numbered 20%-1, 20%-2, 20%-3, 20%-4, 20%-5 and 20%-6 are obtained;

(3) the 10%-1 eluting dry extract obtained in step (2) is dissolved with 30 vol. % methanol, and the solution is filtered through a 0.45 μm microporous membrane and preliminarily separated by high-performance liquid chromatography; the mobile phase is methanol-water 22:78, the flow rate is 1 ml/min, the detection wavelength is 210 nm; chromatographic peaks with retention time of 3-9 min, 9-11 min, 19-22 min, 22-26 min, 26-30 min, 37-41 min and 44-48 min are collected, and the solvent is recovered under reduced pressure, and the following separations are performed respectively (the objects of separation here are the samples from the fractions corresponding to each chromatographic peak with retention time after solvent recovery; 3-9 min chromatographic peak, 9-11 min chromatographic peak, 19-22 min chromatographic peak, 22-26 min chromatographic peak, 26-30 min chromatographic peak, 37-41 min chromatographic peak, and 44-48 min chromatographic peak appearing below respectively correspond to the fractions of the numbers in turn: fraction 3-9, fraction 9-11, fraction 19-22, fraction 22-26, fraction 26-30, fraction 37-41, fraction 44-48):

the sample which is from the fraction corresponding to 3-9 min chromatographic peak after solvent recovery, is further purified by high performance liquid chromatography, mobile phase: methanol-water, 5:95, flow rate: 10 ml/min, detection wavelength 210 nm, chromatographic column: YMC-Pack R & D ODS-A, 250×20 mm, S-10 μm; under these conditions, the fraction corresponding to the chromatographic peak with retention time of 25-27 min is collected, and the solvent is recovered under reduced pressure to obtain compound 14: Cornoside;

the sample which is from the fraction corresponding to 9-11 min chromatographic peak after solvent recovery, is further purified by high performance liquid chromatography, mobile phase: methanol-water, 12:88, flow rate: 10 ml/min, detection wavelength 210 nm, chromatographic column: YMC-Pack R & D ODS-A, 250×20 mm, S-10 μm; under these conditions, the fraction corresponding to the chromatographic peak with retention time of 32-35 min is collected, and the solvent is recovered under reduced pressure to obtain compound 10: Ferruginoside B;

the sample which is from the fraction corresponding to 19-22 min chromatographic peak after solvent recovery, is further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 μm; under these conditions, the fraction corresponding to the chromatographic peak with a retention time of 31-35 min is collected, and the solvent is recovered under reduced pressure to obtain compound 9: Forsythoside E;

the sample which is from the fraction corresponding to 22-26 min chromatographic peak after solvent recovery, is further purified by high performance liquid chromatography, mobile phase: methanol-water, 16:84, flow rate: 10 ml/min, detection wavelength 210 nm, chromatographic column: YMC-Pack R & D ODS-A, 250×20 mm, S-10 μm; under these conditions, the fraction corresponding to the chromatographic peak with a retention time of 32-37 min is collected, and the solvent is recovered under reduced pressure to obtain compound 18: 3,4-dihydroxybenzaldehyde;

the sample which is from the fraction corresponding to 26-30 min chromatographic peak after solvent recovery, is further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 μm; under these conditions, the fraction corresponding to the chromatographic peak with a retention time of 38-42 min is collected, and the solvent is recovered under reduced pressure to obtain a mixture of compound 11: D-Amygdalin and compound 12: L-Amygdalin;

the sample which is from the fraction corresponding to 37-41 min chromatographic peak after solvent recovery, is further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 μm; under these conditions, the fraction corresponding to the chromatographic peak with a retention time of 52-56 min is collected, and the solvent is recovered under reduced pressure to obtain compound 13: Sambunigrin;

the sample which is from the fraction corresponding to 44-48 min chromatographic peak after solvent recovery, is further purified by high performance liquid chromatography, mobile phase: methanol-water, 22:78, flow rate: 10 ml/min, detection wavelength 210 nm, chromatographic column: YMC-Pack R & D ODS-A, 250×20 mm, S-10 μm; under these conditions, the fraction corresponding to the chromatographic peak with a retention time of 41-44 min is collected, and the solvent is recovered under reduced pressure to obtain compound 15: 4-Hydroxy-4-methylenecarbomethoxy-cyclohexa-2,5-dienone;

(4) the 20%-2 eluting dry extract obtained in step (2) is dissolved in 30 vol. % methanol and filtered through a 0.45 μm microporous filter membrane, and the high-performance liquid chromatography is used for preliminary separation; the mobile phase is methanol-water, 22:78, flow rate: 10 ml/min, detection wavelength 210 nm, chromatographic column: YMC-Pack R & D ODS-A, 250×20 mm, S-10 μm; the fractions corresponding to chromatographic peaks with retention time of 14-17 min, 17-19 min, 22-24 min, 29-34 min, and 35-40 min are collected respectively, and the solvent is recovered under reduced pressure, and the following separations are performed respectively (the object of separation here are the sample which is from the fraction corresponding to each chromatographic peak with retention time after solvent recovery; 14-17 min chromatographic peak, 17-19 min chromatographic peak, 22-24 min chromatographic peak, 29-34 min chromatographic peaks, and 35-40 min chromatographic peaks appearing below respectively correspond to the fractions of the numbers in turn: fraction 14-17, fraction 17-19, fraction 22-24, fraction 29-34, fraction 35-40):

the sample which is from the fraction corresponding to 14-17 min chromatographic peak after solvent recovery, is further purified by high performance liquid chromatography, mobile phase: acetonitrile-water, 15:85, flow rate: 10 ml/min, detection wavelength 210 nm, chromatographic column: YMC-Pack R & D ODS-A, 250×20 mm, S-10 μm; under these conditions, the fractions correspond to the chromatographic peaks with retention time of 38-40 min and 45-47 min are collected, the solvent in the fraction correspond to 45-47 min chromatographic peaks is recovered under reduced pressure to obtain compound 7: Lianqiaoxingan C; the solvent in the fraction correspond to 38-40 min chromatographic peaks is recovered under reduced pressure and then purified by high performance liquid chromatography, the mobile phase: acetonitrile-water, 13:87, the flow rate: 10 ml/min, and the detection wavelength: 210 nm. 250×20 mm, S-10 μm, under this condition, the fraction correspond to the chromatographic peak with retention time of 52-56 min is collected, and the solvent is recovered under reduced pressure to obtain compound 6: Ferruginoside A;

the sample which is from the fraction corresponding to 17-19 min chromatographic peak after solvent recovery, is further purified by high performance liquid chromatography, mobile phase: acetonitrile-water, 15:85, flow rate: 10 ml/min, detection wavelength 210 nm, chromatographic column: YMC-Pack R & D ODS-A, 250×20 mm, S-10 μm; under these conditions, the fractions correspond to chromatographic peaks with retention time of 28-30 min and 37-44 min are collected, and the solvent is recovered under reduced pressure to obtain compound 16: Liriodendrin and compound 2: Forsythoside I respectively;

the sample which is from the fraction corresponding to 22-24 min chromatographic peak after solvent recovery, is further purified by high performance liquid chromatography, mobile phase: acetonitrile-water, 17:83, flow rate: 10 ml/min, detection wavelength 210 nm, chromatographic column: YMC-Pack R & D ODS-A, 250×20 mm, S-10 μm; under these conditions, the fraction correspond to the chromatographic peak with a retention time of 22-25 min is collected, and the solvent is recovered under reduced pressure to obtain compound 8: Calceolarioside C;

the sample which is from the fraction corresponding to 29-34 min chromatographic peak after solvent recovery under reduced pressure, white solids are precipitated after the solvent being evaporated during the standing process, and centrifuged at 5000 rpm to obtain compound 17: glycyrrhizin-7-O-β-D-glucoside; the supernatant obtained by centrifugation is further purified by high performance liquid chromatography, mobile phase: acetonitrile-water, 16:84, flow rate: 10 ml/min, detection wavelength 210 nm, chromatographic column: YMC-Pack R & D ODS-A, 250×20 mm, S-10 μm; under these conditions, the fraction correspond to the chromatographic peak with retention time of 40-45 min is collected, and the solvent is recovered under reduced pressure to obtain compound 3: Forsythoside H;

the sample which is from the fraction corresponding to 35-40 min chromatographic peak after solvent recovery, is further purified by high performance liquid chromatography, mobile phase: acetonitrile-water, 16:84, flow rate: 10 ml/min, detection wavelength 210 nm, chromatographic column: YMC-Pack R & D ODS-A, 250×20 mm, S-10 μm; under these conditions, the fraction correspond to the chromatographic peak with retention time of 34-45 min is collected, and the solvent is recovered under reduced pressure to obtain compound 1: Forsythoside A;

(5) the fraction 20%-4 and fraction 20%-5 obtained in step (2) are mixed, and is dissolved with 30 vol. % methanol and filtered through a 0.45 μm microporous membrane, and the high-performance liquid chromatography is used for preliminary separation; mobile phase: acetonitrile-water, 15:85, flow rate: 15 ml/min, detection wavelength 210 nm, chromatographic column: YMC-Pack R & D ODS-A, 250×20 mm, S-10 μm; the fractions correspond to chromatographic peaks with retention time of 15-17 and 35-40 min are collected, and the solvent is recovered under reduced pressure; wherein, the sample which is from the fraction corresponding to 15-17 min chromatographic peak after solvent recovery, is further purified by high performance liquid chromatography, mobile phase: acetonitrile-water, 15:85, flow rate: 12 ml/min, detection wavelength 210 nm, chromatographic column: YMC-Pack R & D ODS-A, 250×20 mm, S-10 μm; under these conditions, the fraction correspond to the chromatographic peak with retention time of 15-16 min is collected, and the solvent is recovered under reduced pressure to obtain compound 5: Isolugrandoside;

the sample which is from the fraction corresponding to 35-40 min chromatographic peak after solvent recovery, is further purified by high performance liquid chromatography, mobile phase: methanol-water, 25:75, flow rate: 12 ml/min, detection wavelength 210 nm, chromatographic column: YMC-Pack R & D ODS-A, 250×20 mm, S-10 μm; under these conditions, the fraction correspond to the chromatographic peak with retention time of 26-29 min is collected, and the solvent is recovered under reduced pressure to obtain compound 4: Lugrandoside.

In some preferred embodiments, in the step (1), the amounts of the water, 10% ethanol, and 30% ethanol used as the eluent are 40 ml water for 1 g of the total extract of Chinese medicine composition, 17.6 ml 10% ethanol for 1 g of the total extract of Chinese medicine composition, 45 ml 30% ethanol for 1 g of the total extract of Chinese medicine composition.

In some preferred embodiments, the amount of the reversed-phase silica gel ODS-AQ-HG in step (2) is: 8 g of the reversed-phase silica gel ODS-AQ-HG for 1 g of 30% ethanol extract obtained in step (1), wherein 3 g of the reversed-phase silica gel ODS-AQ-HG is used for mixing with 1 g of 30% ethanol extract obtained in step (1), and the remaining 5 g is used as the packing for the medium pressure separation column.

Preferably, in step (2), successively 10% methanol and 20% methanol are used to elute; when eluting with 10% methanol, 5 fractions are obtained in order of elution, and the amount of eluent for each fraction is: 66.7 ml of 10% methanol for 1 g of 30% ethanol extract obtained in step (1); when eluting with 20% methanol, 6 fractions are obtained in order of elution, and the amount of eluent for each fraction is: 44.4-66.7 ml of 20% methanol for 1 g of 30% ethanol extract obtained in step (1).

In some embodiments, the traditional Chinese medicine composition is made from crude drugs with the following part by weight:

Fructus Forsythiae 200, Flos Lonicerae 300, Radix Isatidis 200, Radix et Rhizoma Rhei 40, Herba Pogostemonis 60, Rhizoma Dryopteris Crassirhizomae 300, Radix Rhodiolae 100, menthol 9, Herba Ephedrae 60, Semen Armeniacae Amarum 100, Herba Houttuyniae 200, Radix Glycyrrhizae 100, Gypsum Fibrosum 200.

In some embodiments, the traditional Chinese medicine composition is made from crude drugs with the following part by weight:

Fructus Forsythiae 300, Flos Lonicerae 200, Radix Isatidis 300, Radix et Rhizoma Rhei 60, Herba Pogostemonis 100, Rhizoma Dryopteris Crassirhizomae 200, Radix Rhodiolae 60, menthol 5, Herba Ephedrae 100, Semen Armeniacae Amarum 60, Herba Houttuyniae 300, Radix Glycyrrhizae 60, Gypsum Fibrosum 300.

In some examples, the traditional Chinese medicine composition is made from crude drugs with the following part by weight:

Fructus Forsythiae 278, Flos Lonicerae 294, Radix Isatidis 285, Radix et Rhizoma Rhei 55, Herba Pogostemonis 95, Rhizoma Dryopteris Crassirhizomae 290, Radix Rhodiolae 87, menthol 8.5, Herba Ephedrae 88, Semen Armeniacae Amarum 80, Herba Houttuyniae 284, Radix Glycyrrhizae 95, Gypsum Fibrosum 277.

The total extract of the traditional Chinese medicine composition as described above is made by the following steps:

(1) the crude drugs are weighed according to the weight ratio, chosen for the clean ones and ground;

(2) the Herba Pogostemonis is further ground, and the volatile oil is extracted by adding water, which is 10 times the weight of the Herba Pogostemonis; the extraction time of volatile oil is 8 hours, and then the volatile oil is collected and is reserved for use; after the extract is filtered, the residue is discarded and the filtrate is reserved for use;

(3) Fructus Forsythiae, Herba Ephedrae, Herba Houttuyniae, and Radix et Rhizoma Rhei are extracted with 70 wt % ethanol for 3 times, 2.5 hours each time; wherein the weight of 70% ethanol is 12 times the total weight of the Fructus Forsythiae, Herba Ephedrae, Herba Houttuyniae, and Radix et Rhizoma Rhei; then the extracts are mixed and filtrated, the ethanol is recovered, and the filtrate is reserved for use;

(4) Flos Lonicerae, Gypsum Fibrosum, Radix Isatidis, Rhizoma Dryopteris Crassirhizomae, Radix Glycyrrhizae and Radix Rhodiolae are boiled in water, wherein the weight of water is 12 times the total weight of the Flos Lonicerae, Gypsum Fibrosum, Radix Isatidis, Rhizoma Dryopteris Crassirhizomae, Radix Glycyrrhizae and Radix Rhodiolae; then the Semen Armeniacae Amarum is added and boiled twice, 1 hour each time; the extracts are mixed and filtered, and the filtrate obtained is combined with the filtrate obtained after extracting Herba Pogostemonis in step (2), and condensed into a clear extract having a relative density of 1.10-1.15 at 60° C., and then ethanol is added to adjust alcohol concentration to be 70%, refrigerated (for example, 4° C.), filtered, and the ethanol is recovered until no alcohol taste, the clear extract is obtained and reserved for use;

(5) the clear extract obtained in step (4) is combined with the alcohol extract obtained in step (3), and then condensed into a clear extract having relative density of 1.15-1.20 at 60° C.; dried to obtain total extract and reserved for use.

EXAMPLES

Example 1

The traditional Chinese medicine composition is made from crude drugs with the following part by weight: 20 kg of Fructus Forsythiae, 30 kg of Flos Lonicerae, 20 kg of Radix Isatidis, 4 kg of Radix et Rhizoma Rhei, 6 kg of Herba Pogostemonis, 30 kg of Rhizoma Dryopteris Crassirhizomae, 10 kg of Radix Rhodiolae, 0.9 kg of menthol, 6 kg of Herba Ephedrae, 10 kg of Semen Armeniacae Amarum, 20 kg of Herba Houttuyniae, 10 kg of Radix Glycyrrhizae, 20 kg of Gypsum Fibrosum; the total extract of the traditional Chinese medicine composition is made by the following steps:

(1) the crude drugs were weighed according to the weight ratio, chosen for the clean ones and ground;

(2) the Herba Pogostemonis was further ground, and the volatile oil was extracted by adding water, which was 10 times the weight of the Herba Pogostemonis; the extraction time of volatile oil was 8 hours, and then the volatile oil was collected and was reserved for use; after the extract was filtered, the residue was discarded and the filtrate was reserved for use;

(3) Fructus Forsythiae, Herba Ephedrae, Herba Houttuyniae, and Radix et Rhizoma Rhei were extracted with 70 wt % ethanol for 3 times, 2.5 hours each time; wherein the weight of 70 wt % ethanol was 12 times the total weight of the Fructus Forsythiae, Herba Ephedrae, Herba Houttuyniae, and Radix et Rhizoma Rhei; then the extracts were mixed and filtrated, the ethanol was recovered, and the filtrate was reserved for use;

(4) Flos Lonicerae, Gypsum Fibrosum, Radix Isatidis, Rhizoma Dryopteris Crassirhizomae, Radix Glycyrrhizae and Radix Rhodiolae were boiled in water, wherein the weight of water was 12 times the total weight of the Flos Lonicerae, Gypsum Fibrosum, Radix Isatidis, Rhizoma Dryopteris Crassirhizomae, Radix Glycyrrhizae and Radix Rhodiolae; then the Semen Armeniacae Amarum was added and boiled twice, 1 hour each time; the extracts were mixed and filtered, and the filtrate obtained was combined with the filtrate obtained after extracting Herba Pogostemonis in step (2), and condensed into a clear extract having a relative density of 1.15 at 60° C., and then ethanol was added to adjust alcohol concentration to be 70 wt %, refrigerated under 4° C., filtered, and the ethanol was recovered until no alcohol taste, the clear extract was obtained and reserved for use;

(5) the clear extract obtained in step (4) was combined with the alcohol extract obtained in step (3), and then condensed into a clear extract having relative density of 1.20 at 60° C.; dried to obtain total extract (batch number: B1509001) of the traditional Chinese medicine composition and reserved for use.

The steps of the separation method were as follows:
1. Instruments and Materials Bruker AVIIIHD 600 NMR spectrometer (Bruker, Switzerland);

Agilent NMR VNMRS 600 Nuclear magnetic resonance spectrometer (Agilent, USA);

Synapt G2-S Mass Mass spectrometer (Waters, USA);

Combi Flash Rf Medium-low pressure preparative liquid chromatograph (Teledyne ISCO, USA);

Waters 2489-1525 Preparative liquid chromatograph (Waters, USA);

NU3000 Preparative liquid chromatograph (Jiangsu Hanbang Technology Co., Ltd.);

Milli-Q Pure water purifier (US Millipore company);

AL204 Analysis electronic balance (Mettler Toledo, USA);

AB135-S Analytical electronic balance (Mettler Toledo, USA);

TGL-16G Centrifuge (Shanghai Anting Scientific Instrument Factory);

YMC ODS-A-HG 50 μm Reversed phase silica gel (YMC Japan);

YMC-Pack R & D ODS-A (length 250× diameter 20 mm, filler particle size S-10 μm, Japan YMC Corporation);

AB-8 Macroporous resin (Tianjin Xijinna Environmental Protection Material Technology Co., Ltd.);

The total extract of the pharmaceutical composition in the present invention (Shijiazhuang Yiling Pharmaceutical Co., Ltd., batch number: B1509001);

Chromatographically pure acetonitrile and methanol (Shanghai Adamas Reagent Company);

Unless otherwise specified, the chemical reagents used in the present invention are analytical reagents (Beijing Chemical Plant).

Unless otherwise specified, the selection of the above several liquid chromatographs in the high performance liquid chromatography of the examples is related to the use conditions of the chromatography in the technical solution.

Extraction and Separation (1) The total extract of the pharmaceutical composition in the present invention was 5 kg (batch number: B1509001), which was adsorbed by the AB-8 macroporous resin, and then eluted with 200 liters of water, 88 liters of 10% ethanol, 225 liters of 30% ethanol, 250 liters of 50% ethanol, 150 liters of 70% ethanol and 162 liters of 95% ethanol successively, and then the solvent was recovered to obtain the corresponding extracts, wherein 625.0 g was the 30% ethanol extract.

(2) 90.0 g of the 30% ethanol extract was taken and 270.0 g of reversed-phase silica gel YMC ODS-AQ-HG (S-50 μm) was added to be mixed; after a mixed ODS was naturally dried, the mixed ODS was loaded to the sample column, a Combi Flash Rf medium-low pressure preparative liquid chromatograph was used for separation (separation column size: 49×460 mm, packing: 450 g ODS-AQ-HG (S-50 μm)), and 30 liters of 10% methanol, 32 liters of 20% methanol, 24 liters of 30% methanol, 22 liters of 35% methanol, 18 liters of 40% methanol, 18 liters of 45% methanol, 12 liters of 50% methanol, 10 liters of 70% methanol, and 6 liters of anhydrous methanol were used for eluting, respectively; the solvent was recovered under reduced pressure in each elution part; 5 fractions (the solvent amount of each fraction was 6 liters) were obtained in order of elution in the 10% methanol elution part: 4.5 g eluting dry extract (No. 10%-1), 4.0 g eluting dry extract (No. 10%-2), 3.5 g eluting dry extract (No. 10%-3), 2.0 g eluting dry extract (No. 10%-4), and 0.9 g eluting dry extract (No. 10%-5), respectively; six fractions (the solvent amount of each fraction was 6 liters) were obtained in order of elution in the 20% methanol elution part: 2.4 g eluting dry extract (No. 20%-1), 8.6 g eluting dry extract (No. 20%-2), 3.8 g eluting dry extract (No. 20%-3), 3.1 g eluting dry extract (No. 20%-4), 4.0 g eluting dry extract (No. 20%-5), and 1.7 g eluting dry extract (No. 20%-6), respectively.

(3) 2.5 g eluting dry extract with fraction number 10%-1 was taken, and was dissolved with 30% methanol, and then the solution was filtered through a 0.45 μm microporous filter membrane and preliminarily separated by high performance liquid chromatography (mobile phase: methanol-water, the volume ratio of methanol and water was 22:78, the flow rate was 10 ml/min, the detection wavelength was 210 nm, and the column was YMC-Pack R & D ODS-A (250×20 mm, S-10 μm)); the fractions corresponding to chromatographic peaks with retention time of 3-9 min, 9-11 min, 19-22 min, 22-26 min, 26-30 min, 37-41 min, and 44-48 min were collected respectively, and the solvent was recovered under reduced pressure; the above fractions were purified by high efficient liquid chromatography, and multiple monomer compounds were obtained; the specific separation conditions were as follows:

Separation of compound 14: the sample which was from the fraction corresponding to 3-9 min chromatographic peak after solvent recovery, was further purified by high performance liquid chromatography (mobile phase: methanol-water, methanol to water volume ratio of 5:95, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 25-27 min was collected, and the solvent was recovered under reduced pressure to obtain compound 14 (22 mg).

Separation of compound 10: the sample which was from the fraction corresponding to 9-11 min chromatographic peak after solvent recovery, was further purified by high performance liquid chromatography (mobile phase:methanol-water, methanol:water volume ratio 12:88, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 32-35 min was collected, and the solvent was recovered under reduced pressure to obtain compound 10 (15 mg).

Separation of compound 9: the sample which was from the fraction corresponding to 19-22 min chromatographic peak after solvent recovery, was further purified by high-performance liquid chromatography (mobile phase: methanol-water, methanol to water volume ratio of 18:82, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 31-35 min was collected, and the solvent was recovered under reduced pressure to obtain compound 9 (79 mg).

Separation of compound 18: the sample which was from the fraction corresponding to 22-26 min chromatographic peak after solvent recovery, was further purified by high performance liquid chromatography (mobile phase: methanol-water, methanol to water volume ratio of 16:84, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 32-37 min was collected, and the solvent was recovered under reduced pressure to obtain compound 18 (8 mg).

Separation of compound 11 and compound 12: the sample which was from the fraction corresponding to 26-30 min chromatographic peak after solvent recovery, was further purified by high-performance liquid chromatography (mobile phase: methanol-water, the volume ratio of methanol to water was 18:82, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 38-42 min was collected, and the solvent was recovered under reduced pressure to obtain a mixture of compounds 11 and 12 (159 mg).

Separation of compound 13: the sample which was from the fraction corresponding to 37-41 min chromatographic peak after solvent recovery, was recovered by high-performance liquid chromatography (mobile phase:methanol-water, methanol:water volume ratio 18:82, flow rate: 10 ml)/min, detection wavelength 210 nm, chromatographic column: YMC-Pack R & D ODS-A (250×20 mm, S-10 μm)); under these conditions, the fraction corresponding to the chromatographic peak with a retention time of 52-56 min was collected, and the solvent was recovered under reduced pressure to obtain compound 13 (8 mg).

Separation of compound 15: the sample which was from the fraction corresponding to 44-48 min chromatographic peak after solvent recovery, was further purified by high-performance liquid chromatography (mobile phase:methanol-water, methanol:water volume ratio 22:78, flow rate: 10 ml)/min, detection wavelength 210 nm, chromatographic column: YMC-Pack R & D ODS-A (250×20 mm, S-10 μm)); under these conditions, the fraction corresponding to the chromatographic peak with a retention time of 41-44 min was collected, and the solvent was recovered under reduced pressure to obtain compound 15 (10 mg).

(4) 2.9 g of eluenting dry extract with fraction number 20%-2 was taken, and was dissolved with 30% methanol, and then the solution was filtered through a 0.45 μm microporous filter membrane and preliminarily separated by high-performance liquid chromatography (mobile phase: methanol-water, the volume ratio of methanol and water was 22:78, the flow rate was 10 ml/min, the detection wavelength was 210 nm, and the column was YMC-Pack R & D ODS-A (250×20 mm, S-10 μm); the fractions corresponding to chromatographic peaks with retention time of 14-17 min, 17-19 min, 22-24 min, 29-34 min, and 35-40 min were collected respectively, and the solvent was recovered under reduced pressure; the above fractions were purified by high efficient liquid chromatography, and multiple monomer compounds were obtained; the specific separation conditions were as follows:

Separation of compound 6 and compound 7: the sample which was from the fraction corresponding to 14-17 min chromatographic peak after solvent recovery was further purified by high-performance liquid chromatography (mobile phase: acetonitrile-water, the volume ratio of acetonitrile to water was 15:85, flow rate: 10 ml/min, detection wavelength 210 nm, chromatographic column: YMC-Pack R & D ODS-A (250×20 mm, S-10 μm)); under these conditions, the fractions corresponding to chromatographic peaks with retention time of 38-40 min and 45-47 m in were collected, and the solvent was recovered under reduced pressure to obtain the fractions corresponding to a chromatographic peak of 38-40 min and compound 7 (4 mg); the fraction corresponding to the chromatographic peak of 38-40 min was purified by high performance liquid chromatography (mobile phase: acetonitrile-water, the volume ratio of acetonitrile to water was 13:87, flow rate: 10 ml/min, detection wavelength 210 nm, chromatographic column: YMC-Pack R & D ODS-A (250×20 mm, S-10 μm)); under these conditions, the fraction corresponding to the chromatographic peak at 52-56 min was collected, and the solvent was recovered under reduced pressure to obtain compound 6 (4 mg).

Separation of compound 16 and compound 2: the sample which was from the fraction corresponding to 17-19 min chromatographic peak after solvent recovery was further purified by high performance liquid chromatography (mobile phase: acetonitrile-water, the volume ratio of acetonitrile to water was 15:85, flow rate: 10 ml/min, detection wavelength 210 nm, chromatographic column: YMC-Pack R & D ODS-A (250×20 mm, S-10 μm)); under these conditions, the fractions corresponding to chromatographic peaks with retention time of 28-30 min and 37-44 min were collected, and the solvents were recovered under reduced pressure to obtain compound 16 (3 mg) and compound 2 (117 mg).

Separation of compound 8: the sample which was from the fraction corresponding to 22-24 min chromatographic peak after solvent recovery was further purified by high performance liquid chromatography (mobile phase: acetonitrile-water, acetonitrile to water volume ratio 17:83, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 22-25 min was collected, and the solvent was recovered under reduced pressure to obtain compound 8 (36 mg).

Separation of compound 17 and compound 3: the sample which was from the fraction corresponding to 29-34 min chromatographic peak after solvent recovery under reduced pressure was left at room temperature; after the solvent evaporated, a white solid was precipitated and centrifuged at 5000 rpm to obtain compound 17 (10 mg). The supernatant was further purified by high-performance liquid phase (mobile phase: acetonitrile-water, acetonitrile to water volume ratio of 16:84, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 40-45 min was collected, and the solvent was recovered under reduced pressure to obtain compound 3 (19 mg).

Separation of Compound 1: the sample which was from the fraction corresponding to 35-40 min chromatographic peak was further purified by high performance liquid chromatography (mobile phase: acetonitrile-water, acetonitrile to water volume ratio of 16:84, flow rate: 10 ml/min, detection wavelength 210 nm, chromatographic column: YMC-Pack R & D ODS-A (250×20 mm, S-10 μm)); under these conditions, the fraction corresponding to the chromatographic peak with a retention time of 34-45 min was collected, and the solvent was recovered under reduced pressure to obtain Compound 1 (161 mg).

(5) Separation of compound 4 and compound 5: the fraction numbered 20%-4 and fraction numbered 20%-5 were combined, and 2.0 g of the mixed fraction was dissolved with 30% methanol, and then was filtered through a 0.45 μm microporous filter membrane and preliminarily separated by high performance liquid chromatography (mobile phase: acetonitrile-water, volume ratio of acetonitrile to water: 15:85, flow rate: 15 ml/min, detection wavelength: 210 nm, chromatographic column: YMC-pack R&D ODS-A (250×20 mm, S-10 μm)); under these conditions, the fractions corresponding to chromatographic peaks with retention time of 13-15 min and 15-17 min were collected, respectively, and the solvent was recovered under reduced pressure.

The sample which was from the fraction corresponding to 35-40 min chromatographic peak after solvent recovery was further purified by high performance liquid chromatography (mobile phase: methanol-water, methanol to water volume ratio of 25:75, flow rate: 12 ml/min, detection wavelength 210 nm, chromatographic column: YMC-Pack R & D ODS-A (250×20 mm, S-10 μm)); under these conditions, the fraction corresponding to the chromatographic peak with a retention time of 26-29 min was collected, and the solvent was recovered under reduced pressure to obtain compound 4 (32 mg).

The sample which was from the fraction corresponding to 15-17 min chromatographic peak after solvent recovery was further purified by high performance liquid chromatography (mobile phase: acetonitrile-water, acetonitrile to water volume ratio of 15:85, flow rate: 12 ml/min, detection wavelength 210 nm, chromatographic column: YMC-Pack R & D ODS-A (250×20 mm, S-10 μm)); under these conditions, the fraction corresponding to the chromatographic peak with a retention time of 15-16 min was collected, and the solvent was recovered under reduced pressure to obtain compound 5 (4 mg).

Structure Identification

Compound 1: pale green glassy solid (methanol), ESI-MS m/z: 623.2 [M–H]⁻, and the molecular formula of the compound was determined to be $C_{29}H_{36}O_{15}$ based on NMR data.

$^1$H-NMR (DMSO-$d_6$, 600 MHz) $\delta_H$: 6.63 (1H, d, J=1.9 Hz, H-2), 6.64 (1H, d, J=8.1 Hz, H-5), 6.50 (1H, dd, J=8.1, 1.9 Hz, H-6), 2.69 (2H, m, H-7), 4.31 (1H, d, J=7.8 Hz, H-1'), 4.51 (1H, br s, H-1"), 1.05 (1H, d, J=6.2 Hz, H-6"), 7.05 (1H, br s, H-2'''), 6.77 (1H, d, J=8.1 Hz, H-5'''), 7.00 (1H, br s, H-6'''), 7.50 (1H, d, J=15.8 Hz, H-7'''), 6.26 (1H, d, J=15.8 Hz, H-8''').

$^{13}$C-NMR (DMSO-$d_6$, 150 MHz) $\delta_C$: 129.3 (C-1), 115.6 (C-2), 145.1 (C-3), 143.6 (C-4), 116.4 (C-5), 119.6 (C-6), 35.2 (C-7), 70.4 (C-8), 103.0 (C-1'), 73.1 (C-2'), 73.6 (C-3'), 71.0 (C-4'), 74.0 (C-5'), 66.2 (C-6'), 100.6 (C-1"), 70.7 (C-2"), 70.4 (C-3"), 71.9 (C-4"), 68.5 (C-5"), 17.9 (C-6"), 125.6 (C-1'''), 115.0 (C-2'''), 145.7 (C-3'''), 148.6 (C-4'''), 115.9 (C-5'''), 121.5 (C-6'''), 145.7 (C-7'''), 113.9 (C-8'''), 166.0 (C-9''').

The above hydrogen spectrum characteristics and carbon spectrum data were basically consistent with the report in reference [1], and the compound was identified as Forsythoside A. Compound 2: pale green glassy solid (methanol), ESI-MS m/z: 623.2 [M–H]⁻, and the molecular formula of the compound was determined to be $C_{29}H_{36}O_{15}$ based on NMR data.

$^1$H-NMR (DMSO-$d_6$, 600 MHz) $\delta_H$: 6.62 (1H, d, J=1.8 Hz, H-2), 6.64 (1H, d, J=8.1 Hz, H-5), 6.50 (1H, dd, J=8.1, 1.8 Hz, H-6), 2.69 (2H, m, H-7), 4.35 (1H, d, J=7.7 Hz, H-1'), 4.60 (1H, br s, H-1"), 1.14 (1H, d, J=6.2 Hz, H-6"), 7.05 (1H, br s, H-2'''), 6.77 (1H, d, J=8.0 Hz, H-5'''), 7.01 (1H, dd, J=8.0, 1.7 Hz, H-6'''), 7.47 (1H, d, J=15.8 Hz, H-7'''), 6.28 (1H, d, J=15.8 Hz, H-8''').

$^{13}$C-NMR (DMSO-$d_6$, 150 MHz) $\delta_C$: 129.3 (C-1), 115.6 (C-2), 144.9 (C-3), 143.6 (C-4), 116.4 (C-5), 119.7 (C-6), 35.2 (C-7), 70.3 (C-8), 102.8 (C-1'), 71.5 (C-2'), 77.6 (C-3'), 68.3 (C-4'), 75.2 (C-5'), 66.6 (C-6'), 100.8 (C-1"), 70.8 (C-2"), 70.6 (C-3"), 72.0 (C-4"), 68.5 (C-5"), 18.1 (C-6"), 125.8 (C-1'''), 114.9 (C-2'''), 145.7 (C-3'''), 148.4 (C-4'''), 115.9 (C-5'''), 121.3 (C-6'''), 145.1 (C-7'''), 114.8 (C-8'''), 166.2 (C-9''').

The above hydrogen spectrum characteristics and carbon spectrum data were basically consistent with those reported in reference [1], and the compound was identified as Forsythoside I.

Compound 3: transparent glassy solid (methanol), ESI-MS m/z: 623.2 [M–H]⁻, and the molecular formula of the compound was determined to be $C_{29}H_{36}O_{15}$ based on NMR data.

$^1$H-NMR (DMSO-$d_6$, 600 MHz) $\delta_H$: 6.54 (1H, br s, H-2), 6.55 (1H, d, J=8.2 Hz, H-5), 6.41 (1H, dd, J=8.2, 2.0 Hz, H-6), 2.56 (2H, m, H-7), 4.49 (1H, d, J=8.1 Hz, H-1'), 4.60 (1H, br s, H-1"), 1.14 (1H, d, J=6.8 Hz, H-6"), 7.06 (1H, d, J=1.9 Hz, H-2'''), 6.77 (1H, d, J=8.2 Hz, H-5'''), 7.02 (1H, dd, J=8.2, 1.9 Hz, H-6'''), 7.49 (1H, d, J=15.8 Hz, H-7'''), 6.28 (1H, d, J=15.8 Hz, H-8''').

$^{13}$C-NMR (DMSO-$d_6$, 150 MHz) $\delta_C$: 129.1 (C-1), 115.4 (C-2), 144.8 (C-3), 143.4 (C-4), 116.2 (C-5), 119.5 (C-6), 35.0 (C-7), 69.8 (C-8), 100.2 (C-1'), 73.4 (C-2'), 74.1 (C-3'), 70.6 (C-4'), 75.4 (C-5'), 66.6 (C-6'), 100.7 (C-1"), 70.4 (C-2"), 70.3 (C-3"), 71.9 (C-4"), 68.4 (C-5"), 17.9 (C-6"), 125.6 (C-1'''), 114.9 (C-2'''), 145.5 (C-3'''), 148.3 (C-4'''), 115.8 (C-5'''), 121.2 (C-6'''), 144.8 (C-7'''), 114.2 (C-8'''), 165.6 (C-9''').

The above hydrogen spectrum characteristics and carbon spectrum data were basically consistent with those reported in reference [2], and the compound was identified as Forsythoside H.

Compound 4: transparent glassy solid (methanol), ESI-MS m/z: 639.2 [M–H]⁻, and the molecular formula of the compound was determined to be $C_{29}H_{36}O_{16}$ based on NMR data.

$^1$H-NMR (DMSO-$d_6$, 600 MHz) $\delta_H$: 6.64 (1H, o, H-2), 6.64 (1H, o, H-5), 6.51 (1H, br d, J=7.3 Hz, H-6), 2.69 (2H, m, H-7), 4.31 (1H, d, J=7.5 Hz, H-1'), 4.19 (1H, d, J=7.7 Hz, H-1"), 7.06 (1H, br s, H-2'''), 6.77 (1H, o, H-5'''), 7.01 (1H, d, J=7.1 Hz, H-6'''), 7.49 (1H, d, J=15.8 Hz, H-7'''), 6.26 (1H, d, J=15.8 Hz, H-8''').

$^{13}$C-NMR (DMSO-$d_6$, 150 MHz) $\delta_C$: 129.7 (C-1), 116.8 (C-2), 145.4 (C-3), 140.0 (C-4), 116.3 (C-5), 120.0 (C-6), 35.5 (C-7), 71.7 (C-8), 103.1 (C-1'), 73.9 (C-2'), 74.4 (C-3'), 70.7 (C-4'), 73.7 (C-5'), 68.6 (C-6'), 103.7 (C-1"), 74.0 (C-2"), 77.0 (C-3"), 70.4 (C-4"), 77.3 (C-5"), 61.4 (C-6"), 125.9 (C-1'''), 115.4 (C-2'''), 146.1 (C-3'''), 149.1 (C-4'''), 116.0 (C-5'''), 121.9 (C-6'''), 145.4 (C-7'''), 114.2 (C-8'''), 166.7 (C-9''').

The above carbon spectrum data were basically consistent with the report in reference [3], and the compound was identified as Lugrandoside.

Compound 5: transparent glassy solid (methanol), ESI-MS m/z: 639.2 [M–H]⁻, and the molecular formula of the compound was determined to be $C_{29}H_{36}O_{16}$ based on NMR data.

$^1$H-NMR (DMSO-$d_6$, 600 MHz) $\delta_H$: 6.64 (2H, br s, H-2, 5), 6.52 (1H, dd, J=8.0, 1.7 Hz, H-6), 2.69 (2H, m, H-7), 4.36 (1H, d, J=7.7 Hz, H-1'), 4.25 (1H, d, J=7.7 Hz, H-1"), 7.06 (1H, br s, H-2'''), 6.78 (1H, d, J=7.9 Hz, H-5'''), 7.01 (1H, d, J=7.9 Hz, H-6'''), 7.48 (1H, d, J=15.9 Hz, H-7'''), 6.30 (1H, d, J=15.9 Hz, H-8''').

$^{13}$C-NMR (DMSO-$d_6$, 150 MHz) $\delta_C$: 129.8 (C-1), 116.8 (C-2), 145.3 (C-3), 143.9 (C-4), 116.3 (C-5), 120.1 (C-6), 35.5 (C-7), 70.6 (C-8), 103.0 (C-1'), 71.9 (C-2'), 78.0 (C-3'), 68.3 (C-4'), 75.8 (C-5'), 68.5 (C-6'), 103.8 (C-1"), 74.0 (C-2"), 77.3 (C-3"), 70.5 (C-4"), 77.1 (C-5"), 61.5 (C-6"), 126.1 (C-1'''), 116.0 (C-2'''), 145.4 (C-3'''), 148.7 (C-4'''), 116.3 (C-5'''), 121.7 (C-6'''), 146.0 (C-7'''), 115.2 (C-8'''), 166.6 (C-9''').

The above hydrogen spectrum characteristics and carbon spectrum data were basically consistent with those reported in reference [4], and the compound was identified as Isolugrandoside.

Compound 6: light brown glassy solid (methanol), ESI-MS m/z: 639.2 [M–H]$^-$, and the molecular formula of the compound was determined to be $C_{29}H_{36}O_{16}$ based on NMR data.

$^1$H-NMR (DMSO-$d_6$, 600 MHz) $\delta_H$: 6.55 (1H, br s, H-2), 6.54 (1H, d, J=8.0 Hz, H-5), 6.42 (1H, dd, J=8.0, 1.9 Hz, H-6), 2.56 (2H, m, H-7), 4.49 (1H, d, J=8.1 Hz, H-1'), 4.24 (1H, d, J=7.8 Hz, H-1"), 7.06 (1H, br s, H-2'''), 6.77 (1H, d, J=8.1 Hz, H-5'''), 7.02 (1H, dd, J=8.1, 1.9 Hz, H-6'''), 7.49 (1H, d, J=15.8 Hz, H-7'''), 6.28 (1H, d, J=15.8 Hz, H-8''').

$^{13}$C-NMR (DMSO-$d_6$, 150 MHz) $\delta_C$: 129.3 (C-1), 115.9 (C-2), 145.0 (C-3), 143.5 (C-4), 116.3 (C-5), 119.7 (C-6), 35.1 (C-7), 69.9 (C-8), 100.2 (C-1'), 74.3 (C-2'), 75.8 (C-3'), 70.2 (C-4'), 73.5 (C-5'), 68.4 (C-6'), 103.5 (C-1"), 73.6 (C-2"), 77.0 (C-3"), 70.1 (C-4"), 76.8 (C-5"), 61.2 (C-6"), 125.7 (C-1'''), 115.5 (C-2'''), 145.7 (C-3'''), 148.4 (C-4'''), 115.5 (C-5'''), 121.4 (C-6'''), 145.2 (C-7'''), 115.0 (C-8'''), 165.8 (C-9''').

The above hydrogen spectrum characteristics and carbon spectrum data were basically consistent with those reported in reference [4].

Compound 7: light brown glassy solid (methanol), ESI-MS m/z: 609.2 [M–H]$^-$, and the molecular formula of the compound was determined to be $C_{28}H_{34}O_{15}$ based on NMR data.

$^1$H-NMR (DMSO-$d_6$, 600 MHz) $\delta_H$: 6.63 (1H, brs, H-2), 6.62 (1H, d, J=8.0 Hz, H-5), 6.50 (1H, dd, J=8.0, 2.0 Hz, H-6), 2.69 (2H, m, H-7), 4.33 (1H, d, J=7.7 Hz, H-1'), 4.89 (1H, t, J=9.4 Hz, H-3'), 4.19 (1H, d, J=7.6 Hz, H-1"), 7.05 (1H, br s, H-2"'), 6.77 (1H, d, J=8.0 Hz, H-5"'), 7.01 (1H, dd, J=8.0, 1.9 Hz, H-6"'), 7.47 (1H, d, J=15.7 Hz, H-7"'), 6.29 (1H, d, J=15.7 Hz, H-8"').

$^{13}$C-NMR (DMSO-$d_6$, 150 MHz) $\delta_C$: 129.3 (C-1), 116.5 (C-2), 145.1 (C-3), 143.6 (C-4), 115.9 (C-5), 119.7 (C-6), 35.2 (C-7), 70.3 (C-8), 102.7 (C-1'), 71.5 (C-2'), 77.6 (C-3'), 67.9 (C-4'), 75.4 (C-5'), 68.1 (C-6'), 104.2 (C-1"), 73.4 (C-2"), 76.7 (C-3"), 69.7 (C-4"), 65.8 (C-5"), 125.8 (C-1'''), 114.8 (C-2'''), 145.7 (C-3'''), 148.4 (C-4'''), 115.6 (C-5'''), 121.3 (C-6'''), 145.1 (C-7'''), 114.9 (C-8'''), 166.3 (C-9''').

The characteristics of the above hydrogen spectrum were basically consistent with those reported in reference [5]. The structure of the compound was further confirmed by the two-dimensional spectrum, and the carbon signal was assigned to identify the compound as Lianqiaoxingan C.

Compound 8: light brown glassy solid (methanol), ESI-MS m/z: 609.2 [M–H]$^-$, and the molecular formula of the compound was determined to be $C_{28}H_{34}O_{15}$ based on NMR data.

$^1$H-NMR (DMSO-$d_6$, 600 MHz) $\delta_H$: 6.64 (1H, brs, H-2), 6.63 (1H, d, J=8.0 Hz, H-5), 6.51 (1H, dd, J=8.0, 1.8 Hz, H-6), 2.70 (2H, m, H-7), 3.62, 3.89 (2H, m, H-8), 4.30 (1H, d, J=8.1 Hz, H-1'), 4.64 (1H, t, J=9.8 Hz, H-4'), 4.15 (1H, d, J=7.6 Hz, H-1"), 7.06 (1H, br s, H-2"'), 6.77 (1H, d, J=7.9 Hz, H-5"'), 7.02 (1H, dd, J=7.9, 1.4 Hz, H-6"'), 7.49 (1H, d, J=15.8 Hz, H-7"'), 6.27 (1H, d, J=15.8 Hz, H-8"').

$^{13}$C-NMR (DMSO-$d_6$, 150 MHz) $\delta_C$: 129.3 (C-1), 115.6 (C-2), 145.7 (C-3), 143.6 (C-4), 116.4 (C-5), 119.6 (C-6), 35.2 (C-7), 70.3 (C-8), 102.8 (C-1'), 74.0 (C-2'), 73.6 (C-3'), 71.3 (C-4'), 73.3 (C-5'), 68.2 (C-6'), 103.9 (C-1"), 73.4 (C-2"), 76.5 (C-3"), 69.6 (C-4"), 65.8 (C-5"), 125.6 (C-1'''), 115.0 (C-2'''), 145.0 (C-3'''), 148.6 (C-4'''), 115.9 (C-5'''), 121.6 (C-6'''), 145.8 (C-7'''), 113.9 (C-8'''), 166.3 (C-9''').

The above hydrogen spectrum characteristics and carbon spectrum data were basically consistent with those reported in reference [6]. The carbon and hydrocarbon signals were assigned by two-dimensional nuclear magnetic data, and the compound was identified as Calceolarioside C.

Compound 9: transparent glassy solid (methanol), ESI-MS m/z: 461.2 [M–H]$^-$, and the molecular formula of the compound was determined to be $C_{20}H_{30}O_{12}$ based on NMR data.

$^1$H-NMR (DMSO-$d_6$, 400 MHz) $\delta_H$: 6.59 (1H, d, J=3.2 Hz, H-2), 6.61 (1H, d, J=8.0 Hz, H-5), 6.47 (1H, dd, J=8.0, 2.0 Hz, H-6), 2.64 (2H, t, J=7.6 Hz, H-7), 1.11 (3H, d, J=6.4 Hz, H-6").

$^{13}$C-NMR (DMSO-$d_6$, 100 MHz) $\delta_C$: 129.3 (C-1), 116.3 (C-2), 144.9 (C-3), 143.5 (C-4), 115.5 (C-5), 119.5 (C-6), 35.2 (C-7), 70.1 (C-8), 103.0 (C-1'), 73.4 (C-2'), 76.7 (C-3'), 70.2 (C-4'), 75.4 (C-5'), 67.0 (C-6'), 100.8 (C-1"), 70.7 (C-2"), 70.5 (C-3"), 72.0 (C-4"), 68.4 (C-5"), 18.0 (C-6").

The above hydrogen spectrum characteristics and carbon spectrum data were basically consistent with those reported in reference [7], and the compound was identified as Forsythoside E.

Compound 10: transparent glassy solid (methanol), ESI-MS m/z: 477.2 [M–H]$^-$, and the molecular formula of the compound was determined to be $C_{20}H_{30}O_{13}$ based on NMR data.

$^1$H-NMR (DMSO-$d_6$, 600 MHz) $\delta_H$: 6.60 (1H, d, J=1.8 Hz, H-2), 6.61 (1H, d, J=8.2 Hz, H-5), 6.47 (1H, dd, J=8.2, 1.8 Hz, H-6), 4.15 (1H, d, J=7.8 Hz, H-1'), 4.22 (1H, d, J=7.8 Hz, H-1').

$^{13}$C-NMR (DMSO-$d_6$, 150 MHz) $\delta_C$: 129.3 (C-1), 116.3 (C-2), 144.9 (C-3), 143.5 (C-4), 115.5 (C-5), 119.5 (C-6), 35.1 (C-7), 70.0 (C-8), 102.8 (C-1'), 73.4 (C-2'), 76.7 (C-3'), 69.9 (C-4'), 75.7 (C-5'), 68.4 (C-6'), 103.3 (C-1"), 73.4 (C-2"), 76.9 (C-3"), 70.0 (C-4"), 76.7 (C-5"), 61.0 (C-6").

The above hydrogen spectrum characteristics and carbon spectrum data were basically consistent with those reported in reference [8], and the compound was identified as Ferruginoside B.

Compound 11 and Compound 12 were white powdery solids (methanol), and the nuclear magnetic resonance spectrum showed that the component to be measured was a mixture of a pair of epimers.

Comparing the NMR data with those reported in reference [9], it can be confirmed that this component was a mixture of D-Amygdalin and L-Amygdalin, and the molecular weight of the mixture was ESI-MS m/z: 456.2 [M–H]$^-$.

The NMR data of compound 11 D-Amygdalin was assigned as follows: $^1$H-NMR (DMSO-$d_6$, 400 MHz) $\delta_H$: 7.55 (2H, o, H-4, 8), 7.48 (3H, o, H-5, 6, 7), 5.99 (1H, s, H-2), 4.20-4.60 (2H, o, H-1', 1"); $^{13}$C-NMR (DMSO-$d_6$, 100 MHz) $\delta_C$: 118.9 (C-1), 68.5 (C-2), 133.9 (C-3), 129.6 (C-6), 127.3 (C-5, 7), 129.0 (C-4, 8), 103.7 (C-1'), 73.1 (C-2'), 76.8 (C-3'), 70.1 (C-4'), 76.6 (C-5'), 66.8 (C-6'), 101.6 (C-1"), 73.8 (C-2"), 76.8 (C-3"), 70.1 (C-4"), 76.5 (C-5"), 61.1 (C-6").

The NMR data of compound 12 L-Amygdalin was assigned as follows: $^1$H-NMR (DMSO-$d_6$, 400 MHz) $\delta_H$: 7.55 (2H, o, H-4, 8), 7.48 (3H, o, H-5, 6, 7), 5.99 (1H, s, H-2), 4.20-4.60 (2H, o, H-1', 1"); $^{13}$C-NMR (DMSO-$d_6$, 100 MHz) &: 118.2 (C-1), 69.0 (C-2), 133.8 (C-3), 128.9 (C-4, 8), 127.5 (C-5, 7), 129.6 (C-6), 104.0 (C-1'), 72.9 (C-2'), 76.8 (C-3'), 70.3 (C-4'), 76.5 (C-5'), 67.1 (C-6'), 101.0 (C-1"), 73.6 (C-2"), 76.8 (C-3"), 70.0 (C-4"), 76.2 (C-5"), 61.1 (C-6").

Compound 13: amorphous solid (methanol) ESI-MS m/z: 340.1 [M+HCOO]⁻. The molecular formula of the compound was determined to be $C_{14}H_{17}NO_6$ based on NMR data.

¹H-NMR (DMSO-d$_6$, 600 MHz) $\delta_H$: 7.56 (2H, d, J=7.7 Hz, H-2.6), 7.48 (2H, o, H-3.5), 7.48 (1H, o, H-4), 6.03 (1H, s, H-7), 4.19 (1H, d, J=6.6 Hz, H-1'), 3.70 (1H, br d, J=11.6 Hz, H-6'a), 3.51 (1H, br d, J=11.0 Hz, H-6'b), 3.09 (4H, o, H-2', H-3', H-4', H-5'); ¹³C-NMR (DMSO-d$_6$, 150 MHz) δc: 134.4 (C-1), 128.1 (C-2.6), 129.7 (C-3.5), 130.3 (C-4), 67.3 (C-7), 119.5 (C-8), 101.8 (C-1'), 73.9 (C-2'), 77.2 (C-3'), 70.6 (C-4'), 78.0 (C-5'), 61.8 (C-6').

The above hydrogen spectrum characteristics and carbon spectrum data were basically consistent with those reported in the reference [10], and the compound was identified as Sambunigrin.

Compound 14: amorphous solid (methanol), ESI-MS m/z: 315.1 [M−H]⁻, and the molecular formula of the compound was determined to be $C_{14}H_{20}O_8$ based on NMR data.

¹H-NMR (DMSO-d$_6$, 600 MHz) $\delta_H$: 6.04 (2H, d, J=10.1 Hz, H-2, 6), 6.97 (2H, dd, J=10.1 Hz, 2.6 Hz H-3, 5), 4.07 (1H, d, J=7.8 Hz, H-1'), 1.89 (2H, m, H-1'').

¹³C-NMR (DMSO-d$_6$, 150 MHz) $\delta_C$: 185.3 (C-1), 126.4 (C-2, 6), 153.4 (C-3 or C-5), 153.3 (C-3 or C-5), 67.3 (C-4), 39.7 (C-1'), 63.9 (C-2'), 102.9 (C-1''), 73.4 (C-2''), 76.9 (C-3''), 70.0 (C-4''), 76.7 (C-5''), 61.0 (C-6'').

The above hydrogen spectrum characteristics and carbon spectrum data were basically consistent with those reported in reference [11], and the compound was identified as Cornoside.

Compound 15: amorphous solid (methanol), ESI-MS m/z: 195.1 [M−H]⁻, and the molecular formula of the compound was determined to be $C_{10}H_{12}O_4$ based on NMR data.

¹H-NMR (DMSO-d$_6$, 600 MHz) $\delta_H$: 7.02 (2H, br d, J=10.0 Hz H-2, 6), 6.08 (2H, br d, J=10.0 Hz, H-3, 5), 2.69 (2H, s, H-1'), 4.01 (2H, q, J=14.2 Hz, 7.1 Hz, H-3'), 1.13 (3H, td, J=7.1 Hz, 1.4 Hz, H-4').

¹³C-NMR (DMSO-d$_6$, 150 MHz) $\delta_C$: 185.2 (C-1), 126.8 (C-2, C-6), 151.7 (C-3, C-5), 66.6 (C-4), 44.9 (C-1'), 168.6 (C-2'), 60.2 (C-3'), 14.1 (C-4').

The above hydrogen spectrum characteristics and carbon spectrum data were basically consistent with those reported in reference [12], and the compound was identified as 4-Hydroxy-4-methylenecarbomethoxy-cyclohexa-2,5-dienone.

Compound 16: white crystal (methanol), ESI-MS m/z: 787.2 [M+HCOO]⁻, 765.3 [M+Na]⁺, and the molecular formula of the compound was determined to be $C_{34}H_{46}O_{18}$ by NMR data.

¹H-NMR (DMSO-d$_6$, 600 MHz) $\delta_H$: 3.76 (12H, s, OCH$_3$-2, 2', 6, 6'), 6.66 (4H, s, H-3, 3', 5, 5'), 4.67 (2H, d, J=3.8 Hz, H-7, 7'), 4.20 (2H, m, H-9a, 9'a), 3.83 (2H, dd, J=9.2, 3.4 Hz, H-9β, 9'β).

¹³C-NMR (DMSO-d$_6$, 150 MHz) δc: 137.3 (C-1, 1'), 152.8 (C-2, 2', 6, 6'), 104.3 (C-3, 3', 5, 5'), 133.8 (C-4, 4'), 85.2 (C-7, 7'), 53.7 (C-8, 8'), 71.5 (C-9, 9'), 56.6 (OCH$_3$-2, 2', 6, 6'), 102.8 (C-1'', 1'''), 74.3 (C-2'', 2'''), 77.3 (C-3'', 3'''), 70.0 (C-4'', 4'''), 76.6 (C-5'', 5'''), 61.0 (C-6'', 6'''). The above hydrogen spectrum characteristics and carbon spectrum data were basically consistent with those reported in reference [13, 14], and the compound was identified as Liriodendrin.

Compound 17: white powder (methanol), ESI-MS m/z: 417.1 [M−H]⁻, and the molecular formula of the compound was determined to be $C_{21}H_{22}O_9$ based on NMR data.

¹H-NMR (DMSO-d$_6$, 600 MHz) $\delta_H$: 5.53 (1H, dd, J=12.7, 2.8 Hz, H-2), 7.65 (1H, d, J=8.6 Hz, H-5), 6.35 (1H, d, J=2.2 Hz, H-8), 6.51 (1H, dd, J=8.6, 2.2 Hz, H-6), 7.45 (2H, d, J=8.7 Hz, H-2', 6'), 7.07 (2H, d, J=8.8 Hz, H-3', 5'), 3.15 (1H, o, H-3a) 2.68 (1H, dd, J=16.7, 2.9 Hz, H-3b), 3.2-3.5 (4H, m, 2'', 3'', 4'', 5''), 4.89 (1H, d, J=7.5 Hz, H-6''a), 3.70 (1H, d, J=12.0 Hz, H-6''b). ¹³C-NMR (DMSO-d$_6$, 150 MHz) $\delta_C$: 78.8 (C-2), 43.3 (C-3), 190.0 (C-4), 132.5 (C-5), 110.7 (C-6), 164.8 (C-7), 113.6 (C-8), 163.2 (C-9), 102.7 (C-10), 128.5 (C-1'), 128.1 (C-2', 6'), 116.3 (C-3', 5'), 157.6 (C-4'), 100.4 (C-1''), 73.3 (C-2''), 76.7 (C-3''), 69.8 (C-4''), 77.2 (C-5''), 60.8 (C-6'').

The above hydrogen spectrum characteristics and carbon spectrum data were basically consistent with the report in reference [15], and the compound was identified as glycyrrhizin-7-O-β-D-glucoside.

Compound 18: light yellow amorphous solid (methanol), ESI-MS m/z: 137.0 [M−H]⁻, and the molecular formula of the compound was determined to be $C_7H_6O_3$ based on the NMR data.

¹H-NMR (DMSO-d$_6$, 600 MHz) $\delta_H$: 9.68 (CHO), 7.22 (1H, br s, H-2), 6.89 (1H, d, J=8.4 Hz, H-3), 7.25 (1H, br d, J=7.8 Hz, H-4).

¹³C-NMR (DMSO-d$_6$, 150 MHz) $\delta_C$: 191.1 (CHO), 128.8 (C-1), 115.5 (C-2), 145.9 (C-3), 152.2 (C-4), 114.3 (C-5), 124.5 (C-6).

The above hydrogen spectrum characteristics and carbon spectrum data were basically consistent with the reports in reference [16, 17], and the compound was identified as 3,4-dihydroxybenzaldehyde.

Example 2

The traditional Chinese medicine composition is made from crude drugs with the following part by weight: *Fructus Forsythiae* 30 kg, *Flos Lonicerae* 20 kg, *Radix Isatidis* 30 kg, *Radix* et *Rhizoma Rhei* 6 kg, *Herba Pogostemonis* 10 kg, *Rhizoma Dryopteris Crassirhizomae* 20 kg, *Radix Rhodiolae* 6 kg, menthol 0.5 kg, *Herba Ephedrae* 10 kg, *Semen Armeniacae Amarum* 6 kg, *Herba Houttuyniae* 30 kg, *Radix Glycyrrhizae* 6 kg, *Gypsum Fibrosum* 30 kg; the total extract of the traditional Chinese medicine composition was made by the following steps:

(1) the crude drugs were weighed according to the weight ratio, chosen for the clean ones and ground;

(2) the *Herba Pogostemonis* was further ground, and the volatile oil was extracted by adding water, which was 10 times the weight of the *Herba Pogostemonis*; the extraction time of volatile oil was 8 hours, and then the volatile oil was collected and was reserved for use; after the extract was filtered, the residue was discarded and the filtrate was reserved for use;

(3) *Fructus Forsythiae, Herba Ephedrae, Herba Houttuyniae,* and *Radix* et *Rhizoma Rhei* were extracted with 70 wt % ethanol for 3 times, 2.5 hours each time; wherein the weight of 70 wt % ethanol was 12 times the total weight of the *Fructus Forsythiae, Herba Ephedrae, Herba Houttuyniae,* and *Radix* et *Rhizoma Rhei*; then the extracts were mixed and filtrated, the ethanol was recovered, and the filtrate was reserved for use;

(4) *Flos Lonicerae, Gypsum Fibrosum, Radix Isatidis, Rhizoma Dryopteris Crassirhizomae, Radix Glycyrrhizae* and *Radix Rhodiolae* were boiled in water, wherein the weight of water was 12 times of the total weight of the *Flos Lonicerae, Gypsum Fibrosum, Radix Isatidis, Rhizoma Dryopteris Crassirhizomae, Radix Glycyrrhizae* and *Radix Rhodiolae*; then the *Semen Armeniacae Amarum* was added and boiled twice, 1 hour each time; the extracts were mixed and filtered, and the filtrate obtained was combined with the filtrate obtained after extracting *Herba Pogostemonis* in step (2), and condensed into a clear extract having a relative density of 1.10 at 60° C., and then ethanol was added to adjust alcohol concentration to be 70 wt %, refrigerated under 4° C., filtered, and the ethanol was recovered until no alcohol taste, the clear extract was obtained and reserved for use;
(5) the clear extract obtained in step (4) was combined with the alcohol extract obtained in step (3), and then condensed into a clear extract having relative density of 1.15 measured at 60° C.; and dried to obtain the total extract and reserved for use.

The separation method steps were the same as those in Example 1. As a result, the eighteen compounds described in Example 1 were separated.

Example 3

The traditional Chinese medicine composition is made from crude drugs with the following part by weight: 27.8 kg of *Fructus Forsythiae*, 29.4 kg of *Flos Lonicerae*, 28.5 kg of *Radix Isatidis*, 5.5 kg of *Radix et Rhizoma Rhei*, 9.5 kg of *Herba Pogostemonis*, 29 kg of *Rhizoma Dryopteris Crassirhizomae*, 8.7 kg of *Radix Rhodiolae*, 0.85 kg of menthol, 8.8 kg of *Herba Ephedrae*, 8 kg of *Semen Armeniacae Amarum*, 28.4 kg of *Herba Houttuyniae*, 9.5 kg of *Radix Glycyrrhizae*, 27.7 kg of *Gypsum Fibrosum*; the total extract of the traditional Chinese medicine composition was made by the following steps:
(1) the crude drugs were weighed according to the weight ratio, chosen for the clean ones and ground;
(2) the *Herba Pogostemonis* was further ground, and the volatile oil was extracted by adding water, which was 10 times the weight of the *Herba Pogostemonis*; the extraction time of volatile oil was 8 hours, and then the volatile oil was collected and was reserved for use; after the extract was filtered, the residue was discarded and the filtrate was reserved for use;
(3) *Fructus Forsythiae*, *Herba Ephedrae*, *Herba Houttuyniae*, and *Radix et Rhizoma Rhei* were extracted with 70 wt % ethanol for 3 times, 2.5 hours each time; wherein the weight of 70 wt % ethanol was 12 times the total weight of the *Fructus Forsythiae*, *Herba Ephedrae*, *Herba Houttuyniae*, and *Radix et Rhizoma Rhei*; then the extracts were mixed and filtrated, the ethanol was recovered, and the filtrate was reserved for use;
(4) *Flos Lonicerae*, *Gypsum Fibrosum*, *Radix Isatidis*, *Rhizoma Dryopteris Crassirhizomae*, *Radix Glycyrrhizae* and *Radix Rhodiolae* were boiled in water, wherein the weight of water was 12 times of the total weight of the *Flos Lonicerae*, *Gypsum Fibrosum*, *Radix Isatidis*, *Rhizoma Dryopteris Crassirhizomae*, *Radix Glycyrrhizae* and *Radix Rhodiolae*; then the *Semen Armeniacae Amarum* was added and boiled twice, 1 hour each time; the extracts were mixed and filtered, and the filtrate obtained was combined with the filtrate obtained after extracting *Herba Pogostemonis* in step (2), and condensed into a clear extract having a relative density of 1.13 at 60° C., and then ethanol was added to adjust alcohol concentration to be 70 wt %, refrigerated under 4° C., filtered, and the ethanol was recovered until no alcohol taste, the clear extract was obtained and reserved for use;
(5) the clear extract obtained in step (4) was combined with the alcohol extract obtained in step (3), and then condensed into a clear extract having relative density of 1.18 at 60° C.; dried to obtain the total extract and reserved for use.

The separation method steps were the same as those in Example 1. As a result, the eighteen compounds described in Example 1 were separated.

The references mentioned in the examples are as follows:
[1] Fan Yi, Chen Ling, Zhu Jie, et al., Chemical compositions of *Forsythia* leaf [J]. Chinese Journal of Experimental Traditional Medical Formulae, 2015, 12 (24): 22-25.
[2] Wang F N, Ma Z Q, Liu Y, et al., New Phenylethanoid Glycosides from the Fruits of *Forsythia Suspense* (Thunb.) Vahl [J]. *Molecules*, 2009, 14 (3): 1324-1331.
[3] Zheng Xiaoke, Li Jun, Feng Sanitary, et al., Studies on the phenylethanol glycosides of Lithocholic grass [J]. Chinese Traditional and Herbal Drugs, 2002, 33 (10): 19-21.
[4] Lin Sheng, Liu Mingtao, Wang Sujuan, et al., Powder glycosides and phenylethanol glycosides of the *Ligustrum sinense* [J]. China Journal of Traditional Chinese medicine, 2010, 35 (8): 992-996.
[5] Xia Y G, Yang B Y, Liang J, et al., Caffeoyl Phenylethanoid Glycosides from Unripe Fruits of *Forsythia Suspensai* [J]. *CHEM NAT COMPD+*, 2015, 51 (4): 656-659.
[6] Nicoletti M, Galeffi C, Messana I, et al., Phenylpropanoid glycosides from *Calceolaria hypericin* [J]. *Phytochemistry*, 1988, 27 (2): 639-641.
[7] Endo K, Hikino H. Structures of rengyol, rengyoxide and rengyolone, new cyclohexylethane derivatives from *Forsythia suspensa* fruits [J]. *Can. J. Chem.*, 1984, 62 (9): 2011-2014.
[8] Calis I, Tasdemir D, Sticher O, et al., Phenylethanoid Glycosides from *Digitalis. ferruginea* subsp. *farruginea* (=*D. aurea* LiNDLEY)(Scrophulariaceae) [J]. *Chem. Pharm. Bull.*, 1999, 47 (9): 1305-1307.
[9] Xiao Wei, Xie Xue, Song Yaling, et al., Preparation method of Amygdalin: China, CN105461765A [P], 2016-04-06.
[10] Liu Hua, Shen Juanjuan, Zhang Dongming, et al., Studies on the polar components of *Elsholtzia haichowensis* Sun [J]. China Journal of Experimental Traditional Medical Formulae, 2010, 16 (8): 84-86.
[11] Hong M L, Jin K K, Jai M J, et al., Analysis of the inhibitory activity of Abeliophyllum distichum leaf constituents against aldose reductase by using high-speed counter current chromatography[J]. *Arch. Pharm. Res.*, 2013, 36(9): 1104-1112.
[12] Muhammad P, Ahmad S, Nawaz H R, et al., New acetylated quinols from *Ajuga parviflora* [J]. *Fitoterapia*, 1999, 70 (3): 229-232.
[13] Lami N, Kadota S, Kikuchi T, et al., Constituents of the roots of *Boerhaavia diffusa* L. III. Identification of $Ca^{2+}$ channel antagonistic compound from the methanol extract [J]. *Chem. Pharm. Bull.*, 1991, 39 (6): 1551-1555.
[14] He Jun, Zhang Xunjie, Ma Bingzhi, et al., Studies on chemical constituents of *Solanum lyratum thunb* [J]. Chinese Pharmaceutical Journal, 2015, 50 (23): 2035-2038.
[15] Jin Q H, Lee C, Lee J W, et al., Chemical Constituents from the Fruits of *Prunus mume* [J]. *Nat. Prod. Sci.*, 2012, 18 (3): 200-203.
[16] Kang H S, Choi J H, Cho W K, et al., A Sphingolipid and Tyrosinase Inhibitors from the Fruiting Body of *Phellinus linteus* [J]. *Arch. Pharm. Res.*, 2004, 27 (7): 742-750.
[17] Trimbak B M, Tushar M K, Ramakrishna G B. Oxidative decarboxylation of arylacetic acids in water: One-pot transition-metal-free synthesis of aldehydes and ketones[J]. *Tetrahedron Letters*, 2017, 58(29): 2822-2825.

The examples of the present invention have been described above, the above description is exemplary, not exhaustive, and is not limited to the disclosed examples. Many modifications and variations will be apparent to those skilled in the art without departing from the scope and spirit of the various examples described.

The invention claimed is:

1. A method for producing an extract made from combining 200-300 parts of Fructus Forsythiae, 60-100 parts of Herba Ephedrae, 40-60 parts of Radix et Rhizoma *Rhei*, 200-300 parts of Herba Houttuyniae, 200-300 parts of Flos Lonicerae, 200-300 parts of Radix *Isatidis*, 60-100 parts of Herba Pogostemonis, 200-300 parts of Rhizoma Dryopteris Crassirhizomae, 60-100 parts of Radix Rhodiolae, 5-9 parts of menthol, 60-100 parts of Semen Armeniacae *Amarum*, 60-100 parts of Radix Glycyrrhizae, 200-300 parts of Gypsum Fibrosum, wherein the method for producing the extract includes the following steps:
   (1) producing the extract by AB-8 macroporous resin chromatography, and then eluting with water, 10% ethanol, and 30% ethanol in sequence, respectively, and then the 30% ethanol eluate is collected and the solvent is recovered to obtain a 30% ethanol extract;
   (2) the 30% ethanol extract obtained in step (1) is then loaded onto a reversed-phase silica gel ODS-AQ-HG, S-50 um, and mixed; after which a mixed ODS is naturally dried, the mixed ODS is loaded to a sample column, and the medium pressure preparation liquid phase is loaded for separation, the separation column packing is ODS-AQ-HG, S-50 um; successively 10% methanol is used, five fractions are obtained in order of elution, and numbers thereof are 10%-1, 10%-2, 10%-3, 10%-4, 10%-5; 20% methanol are used for eluting, six fractions are obtained in order of elution, and numbers thereof are 20%-1, 20%-2, 20%-3, 20%-4, 20%-5, and 20%-6; the eluate is collected and the solvent is recovered respectively, and eluting dry extracts which are numbered 10%-1, 10%-2, 10%-3, 10%-4, 10%-5 and eluting dry extracts which are numbered 20%-1, 20%-2, 20%-3, 20%-4, 20%-5 and 20%-6 are obtained;
   (3) the 10%-1 eluting dry extract obtained in step (2) is dissolved with 30% methanol, and the solution is filtered through a 0.45 um microporous membrane and preliminarily separated by high-performance liquid chromatography; the mobile phase is methanol-water 22:78, the flow rate is 1 ml/min, the detection wavelength is 210 nm; chromatographic peaks with retention time of 3-9 min, 9-11 min, 19-22 min, 22-26 min, 26-30 min, 37-41 min and 44-48 min are collected, and the solvent is recovered under reduced pressure; and the following separations are performed respectively:
   3-9 min chromatographic peak: being further purified by high performance liquid chromatography, mobile phase: methanol-water, 5:95, flow rate: 10 ml/min, detection wavelength 210 nm, chromatographic column: YMC-Pack R & D ODS-A, 250×20 mm, S-10 um; under these conditions, the chromatographic peak with retention time of 25-27 min is collected, and the solvent is recovered under reduced pressure to obtain compound 14:
   Cornoside;
   9-11 min chromatographic peak: being further purified by high performance liquid chromatography, mobile phase: methanol-water, 12:88, flow rate: 10 ml/min, detection wavelength 210 nm, chromatographic column: YMC-Pack R & D ODS-A, 250×20 mm, S-10 um; under these conditions, the chromatographic peak with retention time of 32-35 min is collected, and the solvent is recovered under reduced pressure to obtain compound 10:
   Ferruginoside B;
   19-22 min chromatographic peak: being further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 um; under these conditions, the chromatographic peak with a retention time of 31-35 min is collected, and the solvent is recovered under reduced pressure to obtain compound 9:
   Forsythoside E;
   22-26 min chromatographic peak: being further purified by high performance liquid chromatography, mobile phase: methanol-water, 16:84, flow rate: 10 ml/min, detection wavelength 210 nm, chromatographic column: YMC-Pack R & D ODS-A, 250×20 mm, S-10 um; under these conditions, the chromatographic peak with a retention time of 32-37 min is collected, and the solvent is recovered under reduced pressure to obtain compound 18: 3,4-dihydroxybenzaldehyde;
   26-30 min chromatographic peak: being further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 um; under these conditions, the chromatographic peak with a retention time of 38-42 min is collected, and the solvent is recovered under reduced pressure to obtain a mixture of compound 11: D-Amygdalin and compound 12: L-Amygdalin;
   37-41 min chromatographic peak: being further purified by high performance liquid chromatography, mobile phase: methanol-water, 18:82, flow rate: 10 ml/min, detection wavelength 210 nm, chromatographic column: YMC-Pack R & D ODS-A, 250×20 mm, S-10 um; under these conditions, the chromatographic peak with a retention time of 52-56 min is collected, and the solvent is recovered under reduced pressure to obtain compound 13:
   Sambunigrin;
   44-48 min chromatographic peak: being further purified by high performance liquid chromatography, mobile phase: methanol-water, 22:78, flow rate: 10 ml/min, detection wavelength 210 nm, chromatographic column: YMC-Pack R & D ODS-A, 250×20 mm, S-10 um; under these conditions, the chromatographic peak with a retention time of 41-44 min is collected, and the solvent is recovered under reduced pressure to obtain compound 15: 4-Hydroxy-4-methylenecarbomethoxy-cyclohexa-2,5-dienone;
   (4) the 20%-2 eluting dry extract obtained in step (2) is dissolved in 30% methanol and filtered through a 0.45 um microporous filter membrane, and high-performance liquid chromatography is used for preliminary separation; mobile phase is methanol-water, 22:78, flow rate: 10 ml/min, detection wavelength 210 nm, chromatographic column: YMC-Pack R & D ODS-A, 250×20 mm, S-10 um; chromatographic peaks with retention time of 14-17 min, 17-19 min, 22-24 min, 29-34 min, and 35-40 min are collected, and the solvent is recovered under reduced pressure, and the following purifications performed respectively:
   14-17 min chromatographic peak: being further purified by high performance liquid chromatography, mobile phase: acetonitrile-water, 15:85, flow rate: 10 ml/min, detection wavelength 210 nm, chromatographic column: YMC-Pack R & D ODS-A, 250×20 mm, S-10 um; under these conditions, the chromatographic peaks with retention time of 38-40 min and 45-47 min are collected, the solvent in 45-47 min chromatographic peaks is recovered under reduced pressure to obtain compound 7: Lianqiaoxingan C; the solvent in 38-40 min chromatographic peaks is recovered under reduced pressure and then purified by high performance liquid chromatography, the mobile phase: acetonitrile-water, 13:87, the flow rate:10 ml/min, and the detection wavelength: 210 nm, chromatographic column: 250×20 mm, S-10 um, under this condition, the chromatographic peak with retention time of 52-56 min is collected, and the solvent is recovered under reduced pressure to obtain compound 6: Ferruginoside A;

17-19 min chromatographic peak: being further purified by high performance liquid chromatography, mobile phase: acetonitrile-water, 15:85, flow rate: 10 ml/min, detection wavelength 210 nm, chromatographic column: YMC-Pack R & D ODS-A, 250×20 mm, S-10 um; under these conditions, chromatographic peaks with retention time of 28-30 min and 37-44 min are collected, and the solvent is recovered under reduced pressure to obtain compound 16: Liriodendrin and compound 2: Forsythoside I respectively;

22-24 min chromatographic peak: being further purified by high performance liquid chromatography, mobile phase: acetonitrile-water, 17:83, flow rate: 10 ml/min, detection wavelength 210 nm, chromatographic column: YMC-Pack R & D ODS-A, 250×20 mm, S-10 um; under these conditions, the chromatographic peak with a retention time of 22-25 min is collected, and the solvent is recovered under reduced pressure to obtain compound 8:

Calceolarioside C;

29-34 min chromatographic peak: after recovering the solvent under reduced pressure, white solids are precipitated during standing process, and centrifuged at 5000 rpm to obtain compound 17: glycyrrhizin-7-O-B-D-glucoside; supernatant is further purified by high performance liquid chromatography, mobile phase: acetonitrile-water, 16:84, flow rate: 10 ml/min, detection wavelength 210 nm, chromatographic column: YMC-Pack R & D ODS-A, 250×20 mm, S-10 um; under these conditions, the chromatographic peak with retention time of 40-45 min is collected, and the solvent is recovered under reduced pressure to obtain compound 3: Forsythoside H;

35-40 min chromatographic peak: being further purified by high performance liquid chromatography, mobile phase: acetonitrile-water, 16:84, flow rate: 10 ml/min, detection wavelength 210 nm, chromatographic column: YMC-Pack R & D ODS-A, 250×20 mm, S-10 um; under these conditions, the chromatographic peak with retention time of 34-45 min is collected, and the solvent is recovered under reduced pressure to obtain compound 1:

Forsythoside A;

(5) the fraction 20%-4 and fraction 20%-5 obtained in step (2) are mixed, and is dissolved with 30% methanol and filtered through a 0.45 um microporous membrane, and high-performance liquid chromatography is used for preliminary separation; mobile phase: acetonitrile-water, 15:85, flow rate: 15 ml/min, detection wavelength 210 nm, chromatographic column: YMC-Pack R & D ODS-A, 250=20 mm, S-10 um;

chromatographic peaks with retention time of 15-17 and 35-40 min are collected, and the solvent is recovered under reduced pressure; wherein, 15-17 min chromatographic peak: being further purified by high performance liquid chromatography, mobile phase: acetonitrile-water, 15:85, flow rate: 12 ml/min, detection wavelength 210 nm, chromatographic column: YMC-Pack R & D ODS-A, 250×20 mm, S-10 um; under these conditions, chromatographic peak with retention time of 15-16 min is collected, and the solvent is recovered under reduced pressure to obtain compound 5:

Isolugrandoside;

35-40 min chromatographic peak: being further purified by high performance liquid chromatography, mobile phase: methanol-water, 25:75, flow rate: 12 ml/min, detection wavelength 210 nm, chromatographic column: YMC-Pack R & D ODS-A, 250×20 mm, S-10 um; under these conditions, the chromatographic peak with retention time of 26-29 min is collected, and the solvent is recovered under reduced pressure to obtain compound 4:

Lugrandoside;

wherein the extract is made by the following steps:
(1) the 200-300 parts of Fructus Forsythiae, 60-100 parts of Herba Ephedrae, 40-60 parts of Radix et Rhizoma *Rhei*, 200-300 parts of Herba Houttuyniae, 200-300 parts of Flos Lonicerae, 200-300 parts of Radix *Isatidis*, 60-100 parts of Herba Pogostemonis, 200-300 parts of Rhizoma Dryopteris Crassirhizomae, 60-100 parts of Radix Rhodiolae, 5-9 parts of menthol, 60-100 parts of Semen Armeniacae *Amarum*, 60-100 parts of Radix Glycyrrhizae, 200-300 parts of Gypsum Fibrosum are weighed;
(2) the Herba Pogostemonis is ground, 10 times the amount of water is added to Herba Pogostemonis and the volatile oil, and extraction time of the volatile oil is 8 hours, and then the volatile oil is collected and is reserved for use; after extract is filtered, the residue is discarded and the filtrate is reserved for use;
(3) Fructus Forsythiae, Herba Ephedrae, Herba Houttuyniae, and Radix et Rhizoma *Rhei* are extracted with 12 the amount of times amount of 70% ethanol for 3 times, 2.5 hours each time; extracts are mixed and filtrated, the ethanol is recovered, and filtrate is reserved for later use;
(4) Flos Lonicerae, Gypsum Fibrosum, Radix *Isatidis*, Rhizoma Dryopteris Crassirhizomae, Radix Glycyrrhizae and Radix Rhodiolae are boiled in 12 times the amount of water, then the Semen Armeniacae *Amarum* is added and boiled twice, one hour each time; extracts are mixed and filtered, and filtrate obtained is combined with the filtrate obtained after extracting Herba Pogostemonis in step (2), and condensing into a clear extract having a relative density of 1.10-1.15 at 60° C., and then ethanol is added to adjust alcohol concentration to be 70%, refrigerated, filtered, and the ethanol is recovered until there is no alcohol taste, the clear extract is then obtained and reserved for use;

there is (5) the clear extract obtained in step (4) is then combined with the alcohol extract obtained in step (3), and then condensed into a clear extract having relative density of 1.15-1.20 at 60° C.; dried to obtain the extract.

* * * * *